United States Patent
Bendall et al.

(10) Patent No.: US 7,170,677 B1
(45) Date of Patent: Jan. 30, 2007

(54) STEREO-MEASUREMENT BORESCOPE WITH 3-D VIEWING

(75) Inventors: Clark A. Bendall, Syracuse, NY (US); Theodore A. Chilek, Auburn, NY (US); Thomas W. Karpen, Skaneateles, NY (US); Raymond A. Lia, Auburn, NY (US); Jon R. Salvati, Skaneateles, NY (US)

(73) Assignee: Everest VIT, Flanders, NJ (US)

( * ) Notice: Subject to any disclaimer, the term of this patent is extended or adjusted under 35 U.S.C. 154(b) by 0 days.

(21) Appl. No.: 10/056,868

(22) Filed: Jan. 25, 2002

(51) Int. Cl.
*G02B 27/22* (2006.01)

(52) U.S. Cl. .................. 359/464; 600/166; 348/49; 348/51; 348/54

(58) Field of Classification Search .............. 359/462, 359/464; 600/101, 166; 348/45, 65, 49, 348/51, 54
See application file for complete search history.

(56) References Cited

U.S. PATENT DOCUMENTS

| | | |
|---|---|---|
| 3,626,828 A | 12/1971 | Lindsey |
| 4,073,569 A | 2/1978 | Rizzo |
| 4,149,773 A | 4/1979 | Reid ................ 359/641 |
| 4,364,629 A | 12/1982 | Lang et al. |
| 4,573,191 A | 2/1986 | Kidode et al. |
| 4,622,954 A | 11/1986 | Arakawa et al. |
| 4,646,723 A | 3/1987 | Arakawa |
| 4,651,201 A | 3/1987 | Schoolman |
| 4,653,855 A | 3/1987 | Birnbach et al. ........... 324/310 |
| 4,682,219 A | 7/1987 | Arakawa |
| 4,741,327 A | 5/1988 | Yabe |
| 4,745,471 A | 5/1988 | Takamura et al. |
| 4,757,805 A | 7/1988 | Yabe |
| 4,772,094 A * | 9/1988 | Sheiman ................ 359/466 |
| 4,773,396 A | 9/1988 | Okazaki |
| 4,779,130 A | 10/1988 | Yabe |

(Continued)

FOREIGN PATENT DOCUMENTS

GB        2 256 992 A        12/1992

(Continued)

OTHER PUBLICATIONS

BioPhotonics In Action; Stereoendoscopy Gives Surgeons Normal Vision; Robert Wood and Wil Cochran; 2 Pages; Sep. 1993.

(Continued)

*Primary Examiner*—Mark A. Robinson
*Assistant Examiner*—Lee Fineman
(74) *Attorney, Agent, or Firm*—Wall Marjama & Bilinski LLP

(57) ABSTRACT

Two stereo images are created by splitting a single image into two images using a field of view dividing splitter. The two images can be displayed side by side so that they can be viewed directly using stereopticon technology, heads-up display, or other 3-D display technology, or they can be separated for individual eye viewing. The two images focus on one imager such that the right image appears on the right side of the monitor and the left image appears on the left side of the monitor. The view of the images is aimed to converge at a given object distance such that the views overlap 100% at the object distance. Measurement is done with at least one onscreen cursor.

66 Claims, 17 Drawing Sheets

U.S. PATENT DOCUMENTS

| | | | |
|---|---|---|---|
| 4,792,694 A | 12/1988 | Shioya et al. | |
| 4,809,680 A | 3/1989 | Yabe | |
| 4,827,909 A | 5/1989 | Kato et al. | |
| 4,832,003 A | 5/1989 | Yabe | |
| 4,862,873 A | 9/1989 | Yajima et al. | |
| 4,868,644 A | 9/1989 | Yabe et al. | |
| 4,871,233 A | 10/1989 | Sheiman | |
| 4,873,572 A | 10/1989 | Miyazaki et al. | 358/98 |
| 4,895,431 A | 1/1990 | Tsujiuchi et al. | |
| 4,918,521 A | 4/1990 | Yabe et al. | |
| 4,926,257 A | 5/1990 | Miyazaki et al. | 358/98 |
| 4,980,763 A | 12/1990 | Lia | 358/98 |
| 4,986,632 A | 1/1991 | Eckmann | |
| 4,996,427 A | 2/1991 | Noble et al. | 250/332 |
| 5,070,401 A | 12/1991 | Salvati et al. | 358/107 |
| 5,122,650 A | 6/1992 | McKinley | |
| 5,191,203 A | 3/1993 | McKinley | |
| 5,222,477 A | 6/1993 | Lia | |
| 5,381,784 A | 1/1995 | Adair | |
| 5,423,312 A | 6/1995 | Siegmund et al. | |
| 5,427,087 A | 6/1995 | Ito et al. | |
| 5,494,483 A | 2/1996 | Adair | |
| 5,522,789 A | 6/1996 | Takahashi | |
| 5,557,323 A | 9/1996 | Kajiwara | |
| 5,557,454 A | 9/1996 | Takahashi | |
| 5,577,991 A | 11/1996 | Akui et al. | |
| 5,588,948 A | 12/1996 | Takahashi et al. | |
| 5,592,328 A * | 1/1997 | Greenberg | 359/389 |
| 5,603,687 A | 2/1997 | Hori et al. | |
| 5,630,784 A | 5/1997 | Siegmund et al. | |
| 5,647,838 A | 7/1997 | Bloomer | |
| 5,649,897 A | 7/1997 | Nakamura et al. | |
| 5,675,378 A | 10/1997 | Takasugi et al. | |
| 5,689,365 A | 11/1997 | Takahashi | |
| 5,694,530 A | 12/1997 | Goto | |
| 5,696,837 A | 12/1997 | Green | |
| 5,701,912 A | 12/1997 | Greening et al. | |
| 5,702,350 A | 12/1997 | Vry et al. | |
| 5,704,791 A | 1/1998 | Gillio | |
| 5,704,897 A | 1/1998 | Truppe | |
| 5,707,340 A | 1/1998 | Hipp et al. | |
| 5,710,428 A * | 1/1998 | Ko | 250/332 |
| 5,720,706 A | 2/1998 | Takahashi et al. | |
| 5,730,129 A | 3/1998 | Darrow et al. | |
| 5,733,246 A | 3/1998 | Forkey | |
| 5,735,290 A | 4/1998 | Sterman et al. | |
| 5,742,429 A | 4/1998 | Tsumanuma et al. | |
| 5,743,846 A | 4/1998 | Takahashi et al. | |
| 5,743,847 A | 4/1998 | Nakamura et al. | |
| 5,747,794 A | 5/1998 | Malchesky | |
| 5,749,362 A | 5/1998 | Funda et al. | |
| 5,749,830 A | 5/1998 | Kaneko et al. | |
| 5,749,892 A | 5/1998 | Vierra et al. | |
| 5,751,341 A | 5/1998 | Chaleki et al. | |
| 5,755,577 A | 5/1998 | Gillio | |
| 5,764,809 A | 6/1998 | Nomami et al. | |
| 5,766,208 A | 6/1998 | McEwan | |
| 5,774,261 A | 6/1998 | Omori et al. | |
| 5,776,049 A | 7/1998 | Takahashi | |
| 5,782,752 A | 7/1998 | Lichtman et al. | |
| 5,784,098 A | 7/1998 | Shoji et al. | |
| 5,791,908 A | 8/1998 | Gillio | |
| 5,793,341 A | 8/1998 | Omori et al. | |
| 5,800,177 A | 9/1998 | Gillio | |
| 5,800,178 A | 9/1998 | Gillio | |
| 5,800,341 A | 9/1998 | McKenna et al. | |
| 5,807,243 A | 9/1998 | Vierra et al. | |
| 5,808,665 A | 9/1998 | Green | |
| 5,810,717 A | 9/1998 | Maeda et al. | |
| 5,817,005 A | 10/1998 | Cohen | |
| 5,817,019 A | 10/1998 | Kawashima | |
| 5,823,958 A | 10/1998 | Truppe | |
| 5,825,532 A | 10/1998 | Mochizuki et al. | |
| 5,825,534 A | 10/1998 | Strähle | |
| 5,828,487 A | 10/1998 | Greening et al. | |
| 5,833,656 A | 11/1998 | Smith et al. | |
| 5,836,954 A | 11/1998 | Heilbrun et al. | |
| 5,840,014 A * | 11/1998 | Miyano et al. | 600/125 |
| 5,840,024 A | 11/1998 | Taniguchi et al. | |
| 5,846,185 A | 12/1998 | Carollo et al. | |
| 5,849,595 A | 12/1998 | Alfano et al. | |
| 5,859,934 A | 1/1999 | Green | |
| 5,860,912 A | 1/1999 | Chiba | |
| 5,861,987 A | 1/1999 | Nakamura et al. | |
| 5,864,359 A | 1/1999 | Kazakevich | |
| 5,871,446 A | 2/1999 | Wilk | |
| 5,876,325 A | 3/1999 | Mizuno et al. | |
| 5,877,732 A | 3/1999 | Ziarati | |
| 5,877,803 A | 3/1999 | Wee et al. | |
| 5,882,206 A | 3/1999 | Gillio | |
| 5,886,675 A | 3/1999 | Aye et al. | |
| 5,886,822 A | 3/1999 | Spitzer | |
| 5,895,350 A | 4/1999 | Hori | |
| 5,914,810 A | 6/1999 | Watts | |
| 5,917,655 A | 6/1999 | Lehnen et al. | |
| 5,919,128 A | 7/1999 | Fitch | |
| 5,924,976 A | 7/1999 | Stelzer et al. | |
| 5,926,318 A | 7/1999 | Hebert | |
| 5,928,137 A | 7/1999 | Green | |
| 5,935,057 A | 8/1999 | Lichtman et al. | |
| 5,941,818 A | 8/1999 | Hori et al. | |
| 5,949,388 A | 9/1999 | Atsumi et al. | |
| 5,951,543 A | 9/1999 | Brauer | |
| 5,953,013 A | 9/1999 | Shimizu | |
| 5,953,114 A | 9/1999 | Spink et al. | |
| 5,953,439 A | 9/1999 | Ishihara et al. | |
| 5,954,634 A | 9/1999 | Igarashi | |
| 5,954,642 A | 9/1999 | Johnson et al. | |
| 5,954,692 A | 9/1999 | Smith et al. | |
| 5,957,832 A | 9/1999 | Taylor et al. | |
| 5,961,456 A | 10/1999 | Gildenberg | |
| 5,964,696 A | 10/1999 | Mihalca et al. | |
| 5,966,168 A | 10/1999 | Miyazaki | |
| 5,971,915 A | 10/1999 | Yamamoto et al. | |
| 5,976,071 A | 11/1999 | Sekiya | |
| 5,976,076 A | 11/1999 | Kolff et al. | |
| 5,983,120 A | 11/1999 | Groner et al. | |
| 5,989,182 A | 11/1999 | Hori et al. | |
| 5,989,185 A | 11/1999 | Miyazaki | |
| 5,995,759 A | 11/1999 | Kohayakawa | |
| 5,999,844 A | 12/1999 | Gombrich et al. | |
| 6,002,430 A | 12/1999 | McCall et al. | |
| 6,005,709 A | 12/1999 | Silver | |
| 6,008,939 A | 12/1999 | Hebert | |
| 6,009,189 A | 12/1999 | Schaack | |
| 6,011,580 A | 1/2000 | Hattori et al. | |
| 6,016,439 A | 1/2000 | Acker | |
| 6,017,304 A | 1/2000 | Vierra et al. | |
| 6,023,632 A | 2/2000 | Wilk | |
| 6,027,476 A | 2/2000 | Sterman et al. | |
| 6,037,939 A * | 3/2000 | Kashiwagi et al. | 715/798 |
| 6,040,946 A | 3/2000 | Hebert | |
| 6,043,890 A | 3/2000 | Spink et al. | |
| 6,043,891 A | 3/2000 | Hartrumpf et al. | |
| 6,059,718 A | 5/2000 | Taniguchi et al. | |
| 6,063,023 A | 5/2000 | Sakiyama et al. | 600/118 |
| 6,066,090 A | 5/2000 | Yoon | |
| 6,075,555 A | 6/2000 | Street | |
| 6,081,371 A | 6/2000 | Shioda et al. | |
| 6,081,740 A | 6/2000 | Gombrich et al. | |
| 6,088,154 A | 7/2000 | Morita | |
| 6,091,453 A | 7/2000 | Coan et al. | |
| 6,094,590 A | 7/2000 | Kan et al. | |
| 6,101,038 A | 8/2000 | Hebert et al. | |

| | | |
|---|---|---|
| 6,104,426 A | 8/2000 | Street |
| 6,104,939 A | 8/2000 | Groner et al. |
| 6,106,456 A | 8/2000 | Storz |
| 6,106,463 A | 8/2000 | Wilk |
| 6,108,005 A | 8/2000 | Starks et al. |
| 6,113,395 A | 9/2000 | Hon |
| 6,115,058 A | 9/2000 | Omori et al. |
| 6,121,999 A | 9/2000 | Schaack |
| 6,122,541 A | 9/2000 | Cosman et al. |
| 6,128,144 A | 10/2000 | Togino |
| 6,137,937 A | 10/2000 | Okano et al. |
| 6,139,490 A | 10/2000 | Breidenthal et al. |
| 6,139,492 A | 10/2000 | Vierra et al. |
| 6,142,932 A | 11/2000 | Morizumi |
| 6,146,390 A | 11/2000 | Heilbrun et al. |
| 6,149,582 A | 11/2000 | Morizumi |
| 6,149,583 A | 11/2000 | Vierra et al. |
| 6,151,164 A | 11/2000 | Greening et al. |
| 6,154,315 A | 11/2000 | Street |
| 6,165,181 A | 12/2000 | Heilbrun et al. |
| 6,166,496 A | 12/2000 | Lys et al. |
| 6,167,296 A | 12/2000 | Shahidi |
| 6,184,923 B1 | 2/2001 | Miyazaki |
| 6,191,809 B1 | 2/2001 | Hori et al. |
| 6,201,648 B1 | 3/2001 | Togino |
| 6,201,984 B1 | 3/2001 | Funda et al. |
| 6,211,626 B1 | 4/2001 | Lys et al. |
| 6,211,904 B1 | 4/2001 | Adair et al. |
| 6,219,182 B1 | 4/2001 | McKinley |
| 6,219,186 B1 | 4/2001 | Hebert |
| 6,221,007 B1 | 4/2001 | Green |
| 6,223,100 B1 | 4/2001 | Green |
| 6,228,055 B1 | 5/2001 | Foerster et al. |
| 6,239,724 B1 | 5/2001 | Doron et al. |
| 6,246,200 B1 | 6/2001 | Blumenkranz et al. |
| 6,246,900 B1 | 6/2001 | Cosman et al. |
| 6,248,074 B1 | 6/2001 | Ohno et al. |
| 6,259,806 B1 | 7/2001 | Green |
| 6,261,226 B1 | 7/2001 | McKenna et al. |
| 6,266,182 B1 | 7/2001 | Morita |
| 6,274,086 B1 | 8/2001 | Wilson et al. |
| 6,275,335 B1 | 8/2001 | Costales |
| 6,309,348 B1 | 10/2001 | Schmidt et al. |
| 6,338,711 B1 | 1/2002 | Sekiya et al. |
| 6,373,523 B1 | 4/2002 | Jang .......................... 348/273 |
| 6,383,131 B1 | 5/2002 | Yamamoto et al. |
| 6,411,327 B1 | 6/2002 | Kweon et al. ................. 348/49 |
| 6,471,642 B1 * | 10/2002 | Igarashi ...................... 600/166 |
| 2002/0082476 A1 | 6/2002 | Takahashi et al. |

FOREIGN PATENT DOCUMENTS

JP   63220217 A * 9/1988

OTHER PUBLICATIONS

Single camera stereo using planar parallel plate; Chunyu Gao and Narendra Ahuja; Beckman Institute, University of Illinois at Urbana-Champaign; 4 Pages.

A Novel Stereo Camera System by a Biprism; DooHyun Lee and InSo Kweon, IEEE Transactions on Robotics and Automation, vol. 16, No. 5, Oct. 2000, pp. 528-541.

A Biprism-Stereo Camera System; Doo Hyun Lee, In So Kweon and Roberto Cipolla, Proceedings of the IEEE Computer Society Conference on Computer Vision and Pattern Recognition (CVPR '99), 6 Pages.

* cited by examiner

STEREO-MEASUREMENT BORESCOPE WITH 3-D VIEWING

FIELD OF THE INVENTION

This invention relates generally to the field of borescopes and endoscopes, and more particularly to a borescope/endoscope which provides a 3-D image from a single camera and lens system.

BACKGROUND OF THE INVENTION

Various devices are known in the prior art for realizing a full color video picture of a target situated within a remote cavity. Most devices of this type employ an external light source conveyed to the image head by fiber optic bundles together with a solid state image sensor and lens system positioned in the distal end of the insertion tube of a borescope/endoscope, referred to herein as a probe, connected to an external video display. A particularly compact head including a light source and solid state image sensor lens system of this type is shown in U.S. Pat. No. 4,491,865 (Danna et al.).

Generally, in systems of this type, the fiber optic illumination bundle and the image sensor and optical system are disposed side by side in the end of a small insertion tube adapted to be inserted in cavities for viewing objects therein. The light provided by the fiber optic bundle has a field of view slightly displaced from the optical field of view of the image sensor, but generally overlapping sufficiently to provide an effective field of vision for the device. The image detected by the image sensor is displayed on a video screen and varies in magnification, apparent size, and detail, depending upon how close the end of the insertion tube carrying the lens system is from the object being viewed. Devices of this type typically have a depth of field from an eighth of an inch (3 mm) to something over four inches (100 mm). The displayed magnification decreases as the distance between the probe tip and the object being viewed increases.

Attempts to measure an object in the image on the video display to determine the size of the object being viewed typically rely on either placing a known scale adjacent to the object to be measured for a comparison measurement, or providing a physical standoff over the lens on the end of the probe insertion tube, at which point the magnification is known and the end of the probe is adjusted until it just touches the object to be viewed at the standoff. With this known magnification, the image can be measured on the screen and the precise size determined. A related method uses optics having a very narrow depth of field and an adjustable focal point. Feedback from the focal point adjustment is used to determine the distance to the in-focus object and therefore the magnification of the object as viewed on the screen. This magnification is then used to perform measurements.

Another measuring system is disclosed in U.S. Pat. No. 4,980,763 (Lia) which measures objects viewed in a borescope by creating an auxiliary structure in the image, such as a shadow, which is projected onto the object so that its position in the video image changes in proportion to the distance of the image sensing head from the object.

U.S. Pat. No. 5,070,401 (Salvati et al.) discloses a 3-D video measurement system in which the depth or thickness of an object is determined along with its length and width. This system relies on the shadow method of the Lia patent to make its 3-D measurements. Although the method works well, it is difficult to achieve optimal shadow positioning and identification in some applications.

Using stereo images for 3-D measurements is becoming popular. U.S. Pat. No. 5,522,789 (Takahashi) discloses a stereo endoscope which includes a pair of objective optical systems, a pair of relay optical systems, an imagery optical system having a single optical axis, and a pair of imaging devices. U.S. Pat. No. 5,860,912 (Chiba) discloses a stereoscopic-vision endoscope system which uses two objective lens systems to provide separate images. The independent lens trains have diverging images so that, even at infinity, the views never overlap 100%. The separate lens trains also create the condition that the right image is displayed on the left side of the monitor and the left image on the right. The separate lens trains are typically very long, on the order of 15–20 mm for a 6 mm diameter probe, thus making the head of the probe very long. U.S. Pat. No. 6,184,923 (Miyazaki) uses a plurality of optical systems in a first detachable tip adapter and a single optical system in a second detachable tip adapter with an endoscope having no optics adjacent to the imager to obtain multiple overlapping fields of view. This approach also typically yields a long distal-tip length and requires a complex attachment mechanism.

SUMMARY OF THE INVENTION

Briefly stated, two stereo images are created by splitting a single image into two images preferably using a field of view dividing splitter. The two images can be displayed side by side so that they can be viewed directly using stereopticon technology, heads-up display, or other 3-D display technology, or they can be separated for individual eye viewing. The two images focus on one imager such that the right image appears on the right side of the monitor and the left image appears on the left side of the monitor. The view of the images is aimed to converge at a given object distance such that the views overlap 100% at the object distance. Measurement is done with an onscreen cursor, a point matching process, and an optical data set.

According to an embodiment of the invention, a device for viewing an object with a probe includes image splitting means for splitting an image of the object into first and second adjacent stereo image parts; image detecting means for detecting the stereo image parts; and focusing means for focusing the two stereo image parts from the image splitting means to the image detecting means; wherein the focusing means includes only one optical axis.

According to an embodiment of the invention, a method for viewing an object with a probe includes the steps of (a) splitting an image of the object into first and second adjacent stereo image parts; (b) detecting the stereo image parts; and (c) focusing the two stereo image parts from the image splitting means to the image detecting means; wherein the step of focusing uses only one optical axis.

DETAILED DESCRIPTION OF THE PREFERRED EMBODIMENT

Figure 1A:
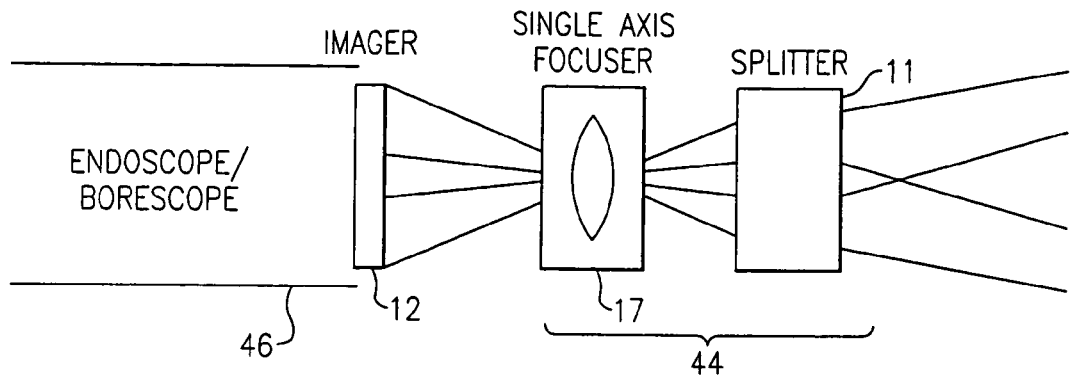
FIG. 1A shows a block diagram of the optical system used in the invention.

Referring to FIG. 1A, a probe 46 contains an imager 12. An optical system 44 includes an image splitter 11 and a single axis focuser 17. Image splitter 11 divides the field of view of focuser 17 into two overlapping fields of view which have different optical axes. The two fields of view are then focused on imager 12 by focuser 17.

Figure 1B:
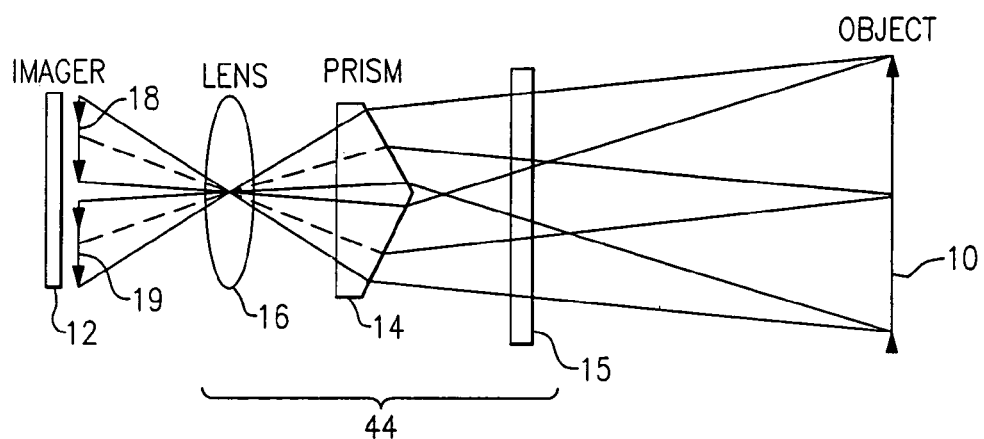
FIG. 1B shows an optical path diagram used in explaining a first embodiment of the invention.
Figure 2:
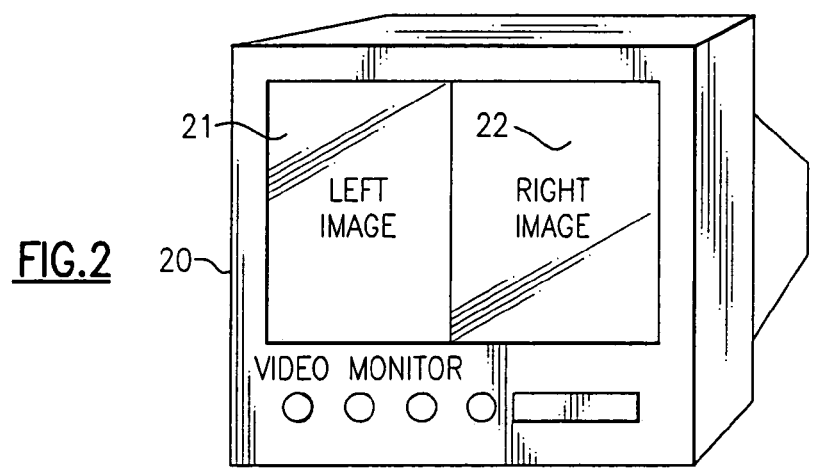
FIG. 2 shows a video monitor operating with the first embodiment of the invention.

Referring to FIGS. 1B–2, an embodiment of optical system 44 shows an object 10 imaged onto imager 12 through a prism 14 and a lens assembly 16. The image of object 10 is split into two stereo image parts 18, 19 by prism 14. Prism 14 is preferably a refractive image-splitting prism, such as, for example, a wedge prism. Image parts 18 and 19 are then displayed on a monitor 20. The geometric dimensions of object 10 are then measured using at least one onscreen cursor along with a measurement process as discussed below. A transparent window 15 is optionally used to prevent fluids from contacting prism 14.

Using a single prism 14 to split the image rather than using two separate lens assemblies simplifies and shortens the length of the optical assembly, while preventing the overlap of image parts 18 and 19 on imager 12 without the use of complex masking. Image parts 18, 19 preferably focus on imager 12 such that a right image 22 appears on the right side of monitor 20 and a left image 21 appears on the left side of monitor 20 without electronic manipulation. The two fields of view created by the splitting prism are aimed to converge at a given object distance such that the views overlap 100% at the object distance. Measurements can only be performed where the views overlap. It is therefore desirable to maximize the overlap within the measurable object-distance range, which is typically from about 5 mm to about 25 mm for a 4 mm to 10 mm diameter probe. By making the fields of view overlap 100% within this range, a larger portion of the image can be used for measurements than if the views overlap 100% outside this range. In the case of parallel or diverging optical axes, the two fields of view never overlap 100%, which makes a large portion of the image unusable for measurements. Mirrors could be used in place of prism 14. Although using mirrors reduces the compression and bending aberrations introduced by prism 14, achieving the same optical separation using mirrors requires a much larger optical assembly than does the equivalent prism. Thus, prism 14 is more desirable for small-diameter probes.

Images 18, 19 are preferably displayed side by side on a video monitor 20 as left and right images 21, 22 for direct 2-D viewing. The images can also be viewed using stereopticon technology, heads-up display, or other 3-D display technology to convey the depth information captured in the stereo image. A single image is optionally displayed, because positioning a probe using the live image with both stereo image parts displayed can be distracting and fatiguing. Displaying only one of the stereo image parts during positioning eliminates the distraction caused by the second image part, thus reducing fatigue.

The index of refraction of the medium contacting the wedged face of prism 14 affects the convergence angle and effective separation of the two fields of view. If the medium has the same index of refraction as the prism material, image splitting does not occur. By adding optional transparent window 15, contact between prism 14 and external media, such as fluids, is prevented thus ensuring that splitting occurs in the desired medium, typically air, and convergence is maintained. The effects of external media between window 15 and object 10 are then limited to increasing the object distance of the 100% overlap point and reducing fields of view.

Figure 3:
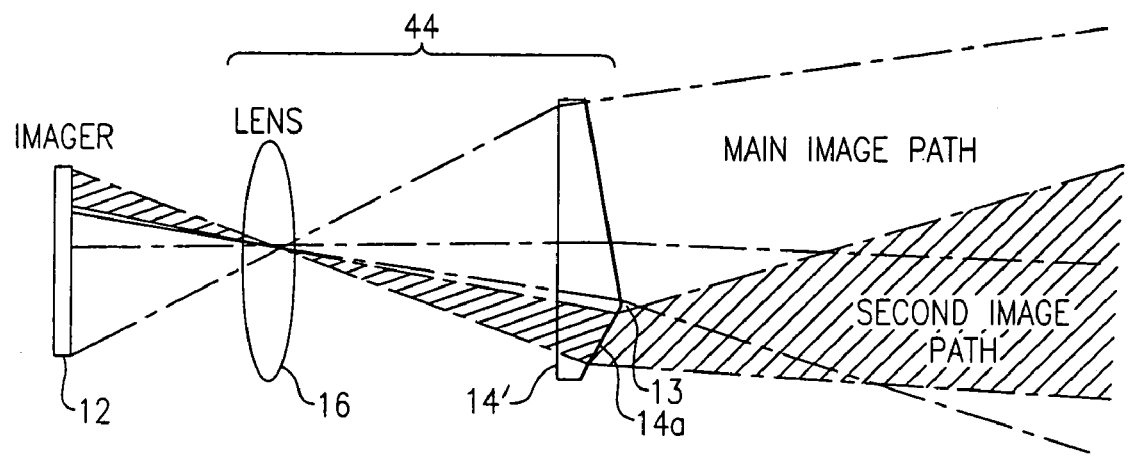
FIG. 3 shows an optical path diagram used in explaining a second embodiment of the invention.
Figure 4:
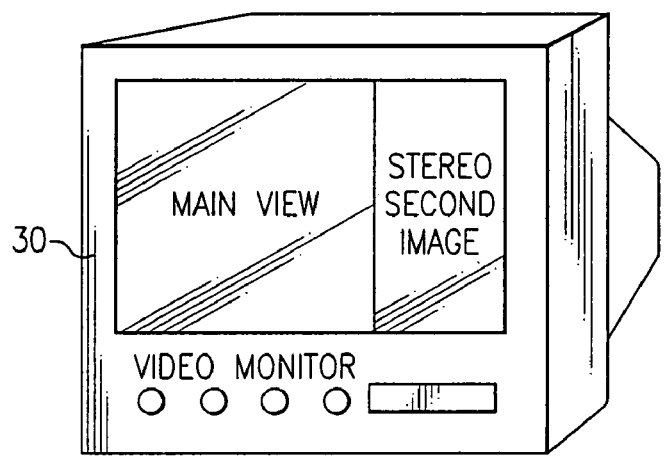
FIG. 4 shows a video monitor operating with the second embodiment of the invention.

Referring to FIGS. 3–4, an alternative embodiment is shown in which stereo optical system 44 includes a non-symmetrical prism 14' on which a ridge 13 is displaced from the center of the optical axis of single-axis lens 16 such that one of the stereo views, the "main image path" in FIG. 3, is imaged onto more than one half of imager 12, while the other stereo view, the "second image path" in FIG. 3, is imaged onto less than one half of imager 12. The magnification and convergence angle of the second image path are controlled by the contour and angle of prism surface 14a. The image provided by the "main image path" is preferably displayed on a monitor 30.

The image provided by the second optical path is used by a computational element to obtain a correlation with the image from the first optical path. This correlated image is used by the computational element, along with data describing the characteristics of the optical system, to determine dimensional parameters of viewed objects and provide measurement results to a display, such as video monitor 30 and/or memory/file/storage, preferably accessible to the user. This system can also be provided with more than two optical paths, such that intersection of the optics for the stereo measurement can be specified for near and far measurement in the same system. The asymmetrical splitting of the image can also be performed with a non-prism based splitter such as a dual lens assembly. The computational element can provide a probability estimate for a successful image to image correlation, and optionally request user input to validate or correct the correlation if the probability falls below a preset level.

The invention provides an automatic system for measuring various parameters of an object being viewed by the above described stereo optical imaging systems without the need for a known scale or optical reference, such as a shadow or laser projection. Using this system, three dimensional measurements can be made of objects viewed by a single, two dimensional image sensor. Measurements are preferably corrected for magnification (left and right), lens distortion, and other factors which would otherwise degrade the accuracy of the measurement results produced by the above mentioned computational element.

A number of systems exist which acquire images from two or three different perspectives. The relative positions of the objects in the different images change based on the distance between the camera and the objects. This change in relative position allows measurements to be performed. One of the most challenging aspects of such systems is identifying matching points in the different images. Many algorithms have been developed to create disparity maps from these images which indicate the distance to points in the images. These algorithms are generally computationally intensive and provide more information than is needed for applications that require only two to four point pairs. Other systems search the images for a good match without any consideration for the global alignment of the images. This often results in incorrect matches when there are repeating patterns or multiple similar points in the images.

The present invention performs a relatively fast, automatic, global alignment prior to matching specific points for measurement. The global alignment is then used to limit the search range on the point-pair matching, thus improving the speed and reliability of the matching process.

Figure 5:
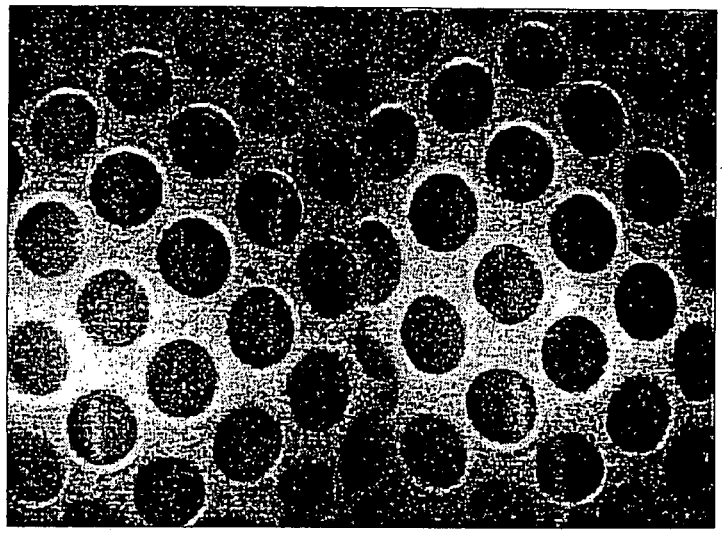
FIG. 5 shows a stereo image in which a repeating pattern exists which creates a high probability of incorrect matches.

Referring to FIG. 5, a stereo image is shown in which a repeating pattern exists which creates a high probability of incorrect matches when global alignment is not taken into consideration. Prior to performing specific point matching, a global alignment is performed. The global alignment consists of obtaining global vertical shift data and regional horizontal shift data. The vertical shift between the left and right images, referred to as the global vertical shift, is caused mainly by optical misalignments and is relatively constant throughout the image. The horizontal shift between the left and right images is dependent on the optical characteristics and the distance from the distal tip of the probe to the surface being viewed, which may vary throughout the image depending on the contour of the surface and the tip orientation. The regional horizontal shift data indicates the horizontal shift at one or more particular positions within the image.

Figure 6:
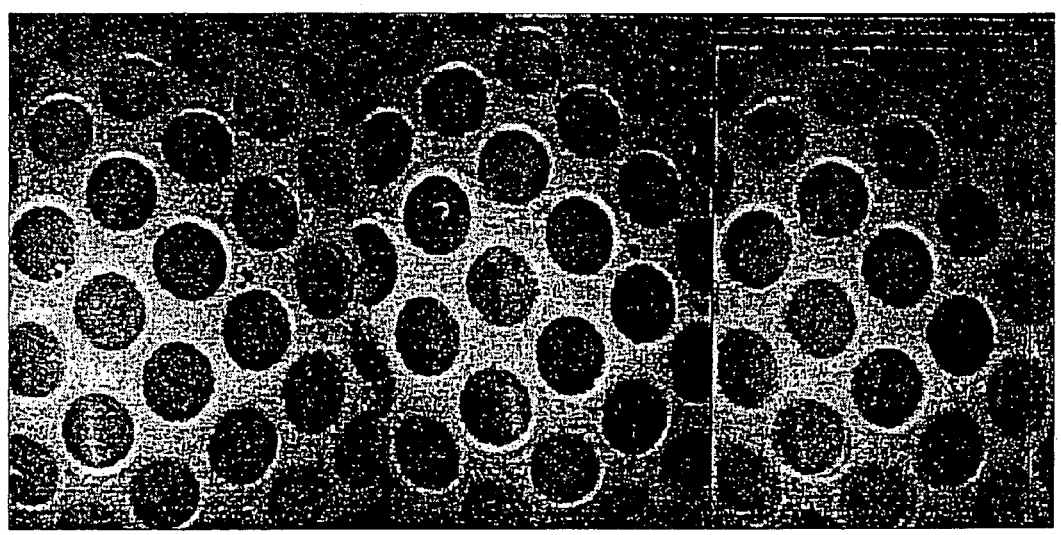
FIG. 6 shows the two images of FIG. 5 superimposed on one another according to an embodiment of the present invention.
Figure 7:
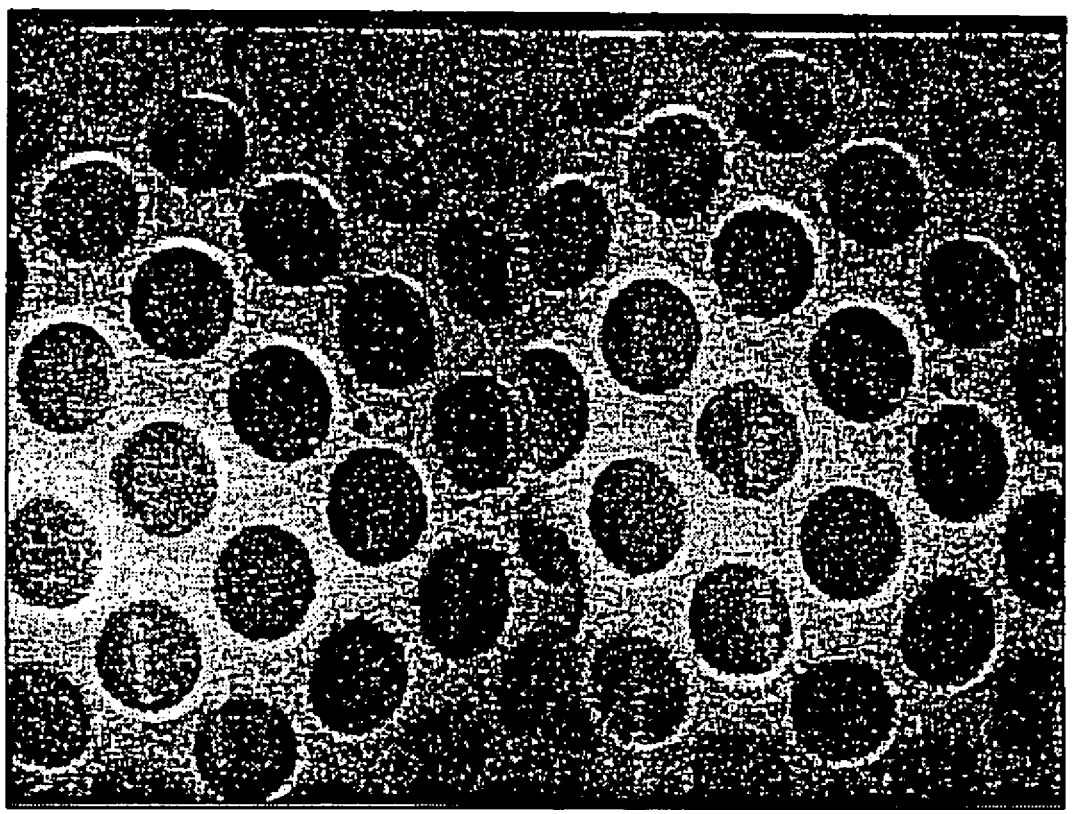
FIG. 7 shows the two images of FIG. 5 with two matched point pairs.

Referring to FIG. 6, the global alignment has been used to create a superimposed view of the two images to the right of the image of FIG. 5. When specific points are then matched, the search area can be reduced based on the global alignment information, thus speeding up the search and reducing the likelihood of incorrect matches. FIG. 7 shows the image with two matched point pairs.

There are two main processes that this approach employs. The first is the global alignment process which is preferably performed as follows.

1) Convert the image to black and white and decimate the image to reduce processing time (optional).

Figure 8:
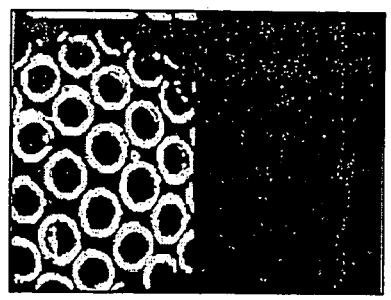
FIG. 8 shows part of an image used in explaining an embodiment of the present invention.

2) Perform edge detection on the left image as shown in FIG. 8.

Figure 9:
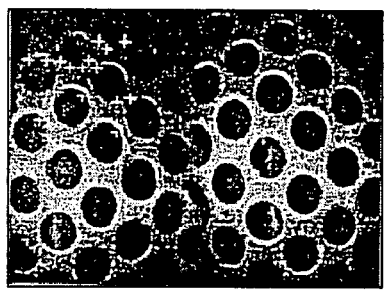
FIG. 9 shows parts of two images used in explaining an embodiment of the present invention.

3) Find multiple edge endpoints or non-straight edge points which are relatively easy to match using simple matching algorithms, as shown by the crosses in the left image of FIG. 9.

Figure 10:
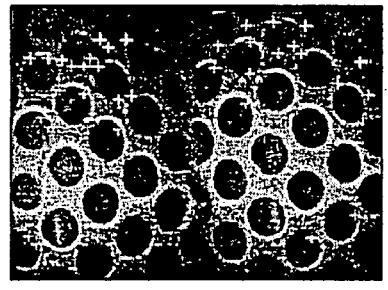
FIG. 10 shows parts of two images used in explaining an embodiment of the present invention.

4) Find matching points in the right image using a standard algorithm such as simple pixel value comparison, shown in FIG. 10.

5) Count the number of times each possible left image to right image vertical shift occurs in the set of matched point pairs.

6) Find the most common, or global, vertical shift. The vertical shift is essentially constant regardless of object distance or position in the image.

7) Attempt to realign points that do not conform well to the global vertical shift.

Figure 11:
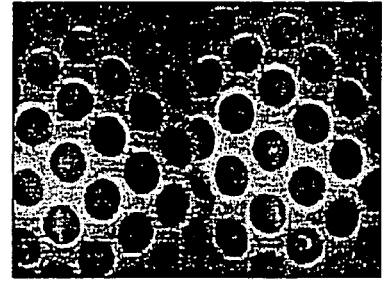
FIG. 11 shows parts of two images used in explaining an embodiment of the present invention.

8) Throw out points that appear to be invalid. The remaining "good" matches are shown as the crosses in FIG. 11. The horizontal shifts between these matched point pairs provide the regional horizontal shift data.

The second step is the matching of the specific points being used for the measurement, preferably performed as follows.

Figure 12:
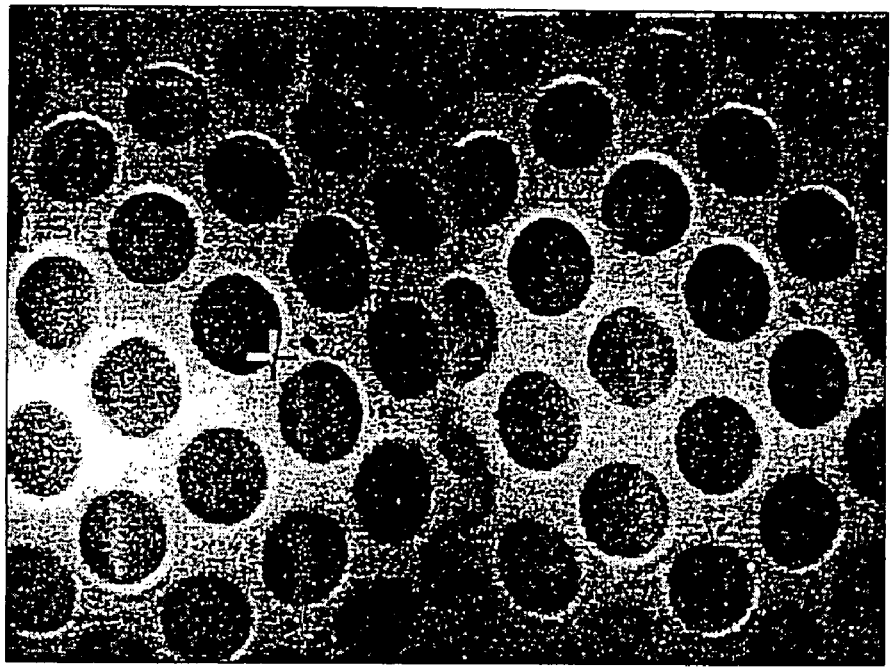
FIG. 12 shows parts of two images used in explaining an embodiment of the present invention.

1) The user identifies a desired point in the left image as shown by the cross in FIG. 12.

Figure 13:
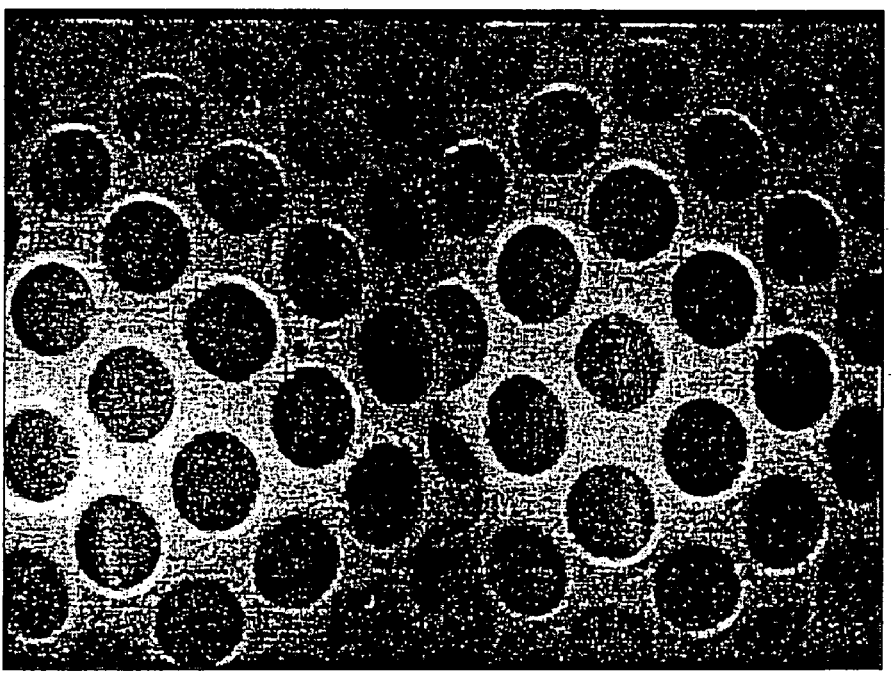
FIG. 13 shows parts of two images used in explaining an embodiment of the present invention.

2) Nearby points are found that were used in the global alignment as shown by the crosses in FIG. 13.

3) The maximum and minimum horizontal shifts of the nearby points are found. The horizontal shift may vary with position depending on the orientation and contour of the target surface.

Figure 14:
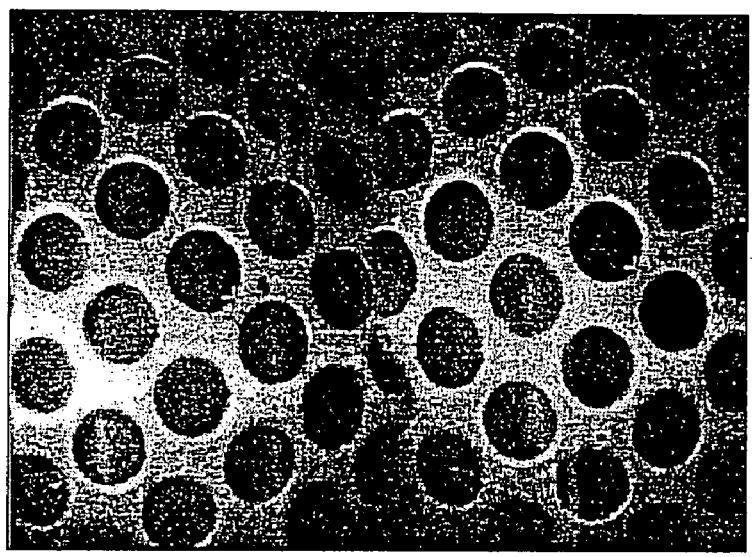
FIG. 14 shows parts of two images used in explaining an embodiment of the present invention.

4) The right image is searched for a match using the above maximum and minimum horizontal shifts along with the global vertical shift to limit the search region. The result is shown in FIG. 14.

The matching process is preferably implemented in software, but implementation in hardware or firmware is possible. The matching process can also be implemented manually or as a combination of manual steps and automatic steps. In a purely manual mode, the user identifies the matched point in both images. If the system cannot automatically find points having only one good match for use in the global alignment step, the user is optionally asked to manually identify a matched point to give the system a starting point for the global alignment. Additionally, if the automatic matching process finds either multiple good matches or no good match for a specific user-identified point, the user is optionally asked to identify the correct match.

Figure 15:
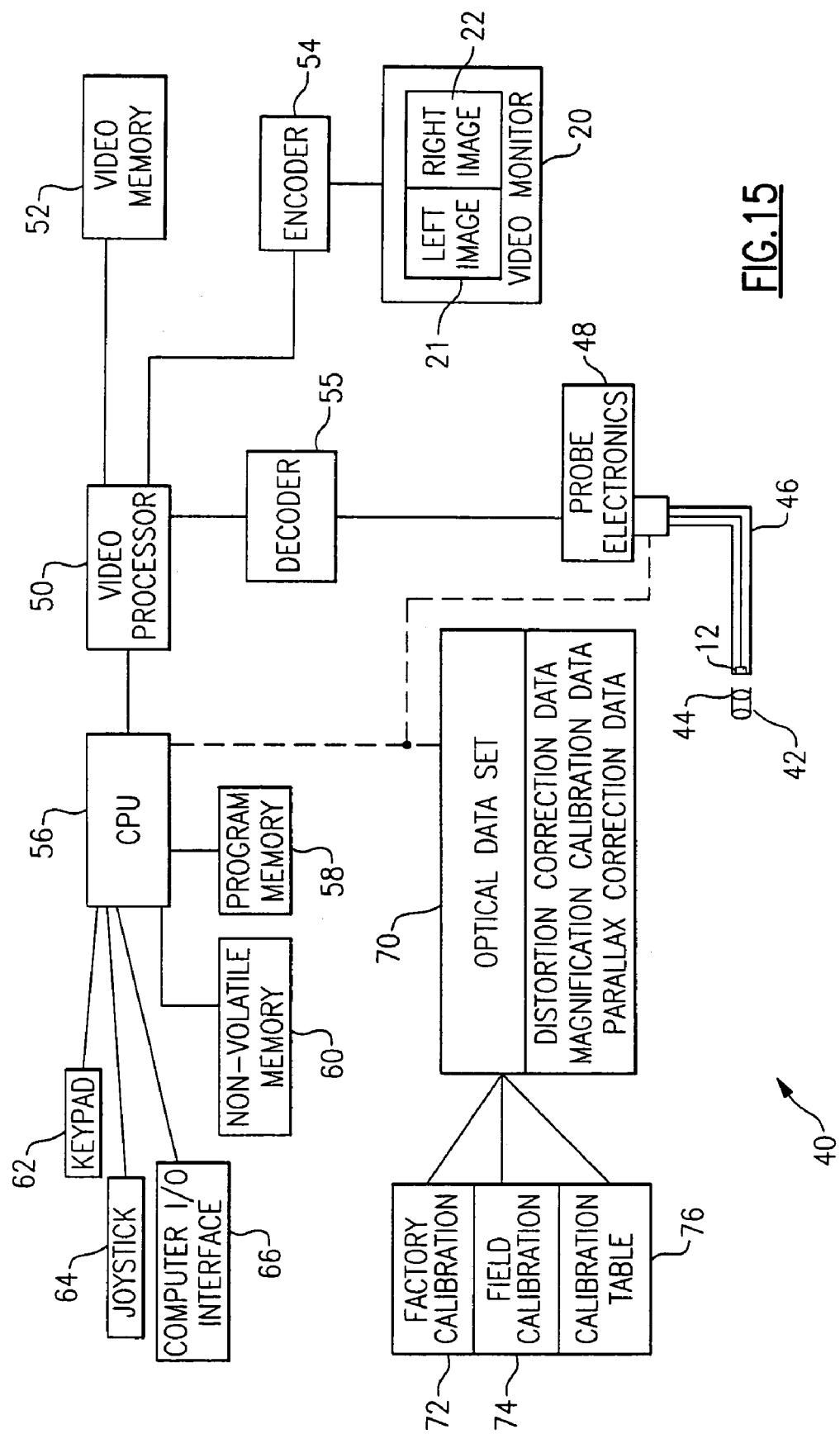
FIG. 15 shows a borescope/endoscope system according to an embodiment of the invention.

Referring to FIG. 15, a borescope/endoscope system 40 according to an embodiment of the invention is shown. A detachable distal tip 42 contains optical system 44. Imager 12 is included in a probe 46. An optical data set 70 describing optical system 44 is generated using either factory calibration 72, field calibration 74, or a fixed calibration table 76. It should be noted that this generated optical data set can further include, for example, color balancing. In addition, the optical characteristics data set can be adjusted so that the probe is operable in a medium, for example, having an index of retraction other than air. Optical data set 70 is preferably stored in non-volatile memory in probe electronics 48 and passed to a CPU 56 for use in stereo measurement. This approach allows probe 46 to be used with different processor boxes without requiring a manual transfer of optical data set 70. Probe electronics 48 also convert the signals from imager 12 to a format accepted by a video decoder 55. Video decoder 55 produces a digitized version of the stereo image produced by probe electronics 48. A video processor 50 stores the digitized stereo image in a video memory 52, while giving CPU 56 access to the digitized stereo image. CPU 56, which preferably uses both a non-volatile memory 60 and a program memory 58, performs the global alignment, point matching, and measurement using the digitized stereo image and optical data set 70. A keypad 62, a joystick 64, and a computer I/O interface 66 preferably convey user input for such functions as cursor movement to CPU 56. Video Processor 50 superimposes graphics such as cursors and results on the digitized image as instructed by CPU 56. An encoder 54 converts the digitized image and superimposed graphics into a video format compatible with monitor 20 on which left image 21, right image 22, and superimposed graphics are displayed.

As precise as manufacturing optics elements has become, every optical device is different. Every optical system 44 is preferably calibrated in conjunction with probe 46, especially when optical system 44 resides in detachable distal tip 42. Optical data set 70 is preferably determined for the probe and optical system combination. Three calibration methods are preferably used to generate optical data set 70. Factory calibration 72 is performed when the probe unit is originally manufactured, as well as when a customer sends the unit back to the factory for calibration. Field calibration 74 is performed outside the factory preferably whenever a new detachable distal tip 42 is placed onto probe 46. Table calibration using a calibration table 76 is optionally used for certain applications. If one assumes a certain similarity of lenses due to very precise manufacturing technologies, one probe and optical system is calibrated, and calibration table 76 is made from the results. Other probes then use the same calibration table 76. Alternatively, calibration table 76 is optionally generated through theoretical analysis of the optical system. For some applications, using calibration table 76 provides adequate calibration accuracy.

Figure 16:
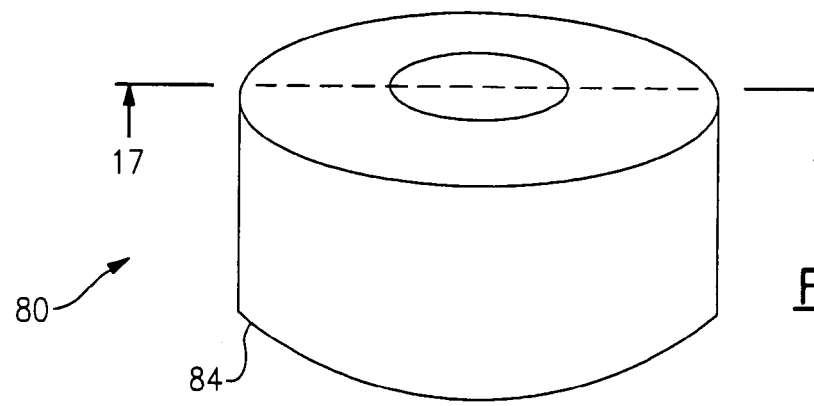
FIG. 16 shows an embodiment of a calibration tool used with an embodiment of the present invention.
Figure 17:
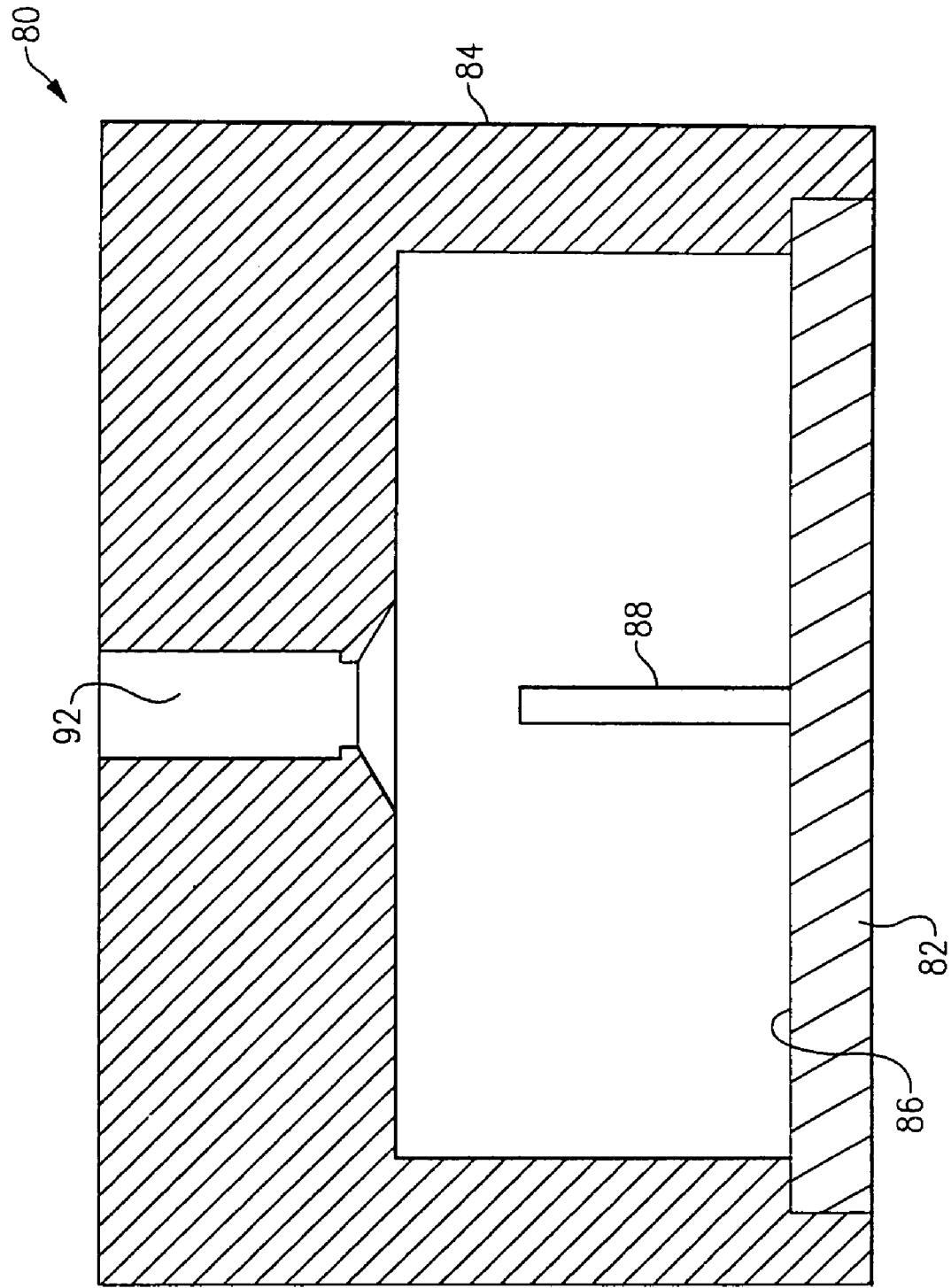
FIG. 17 shows a cross-section taken along the line 17—17 in FIG. 16.

Referring to FIGS. 16–17, a calibration tool 80 is shown. Calibration tool 80 includes a base 82 and a cover 84. Cover 84 preferably fits over base 82 such that part of cover 84 fits against an upper surface 86 of base 82. Base 82 includes a post 88 with a line 94 on top of post 88. A cavity 92 is shaped to receive detachable distal tip 42 attached to probe 46, or in the case of a non-detachable design, the tip of probe 46 containing optical system 44.

Figure 19:
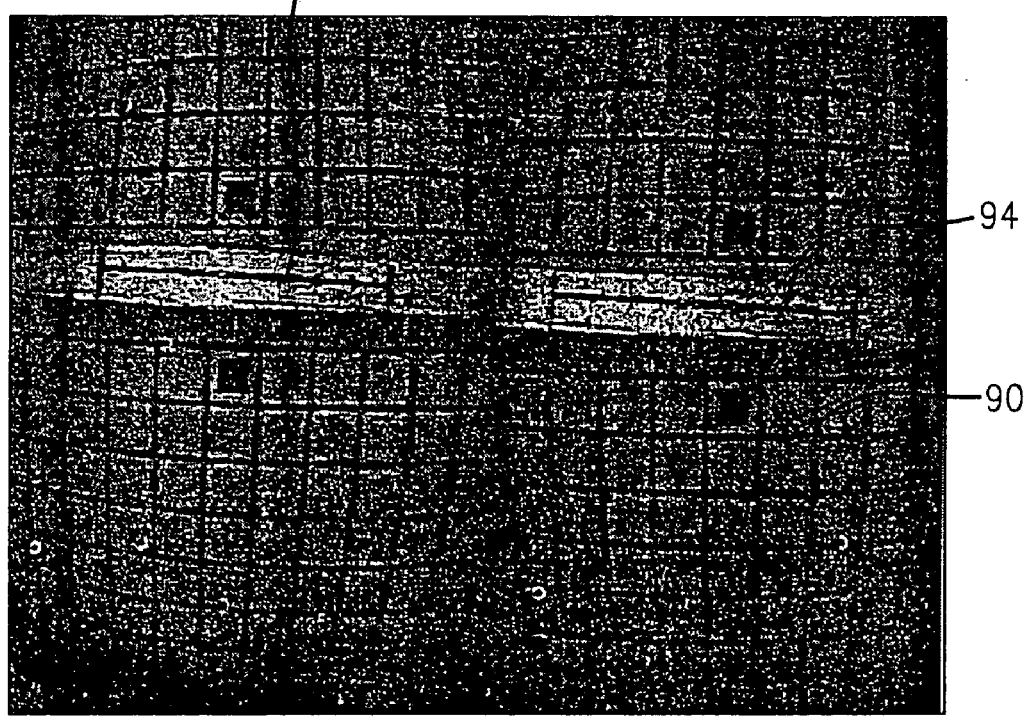
FIG. 19 shows left and right stereo images taken of the base of FIG. 18 through the calibration tool of FIG. 16.
Figure 18:
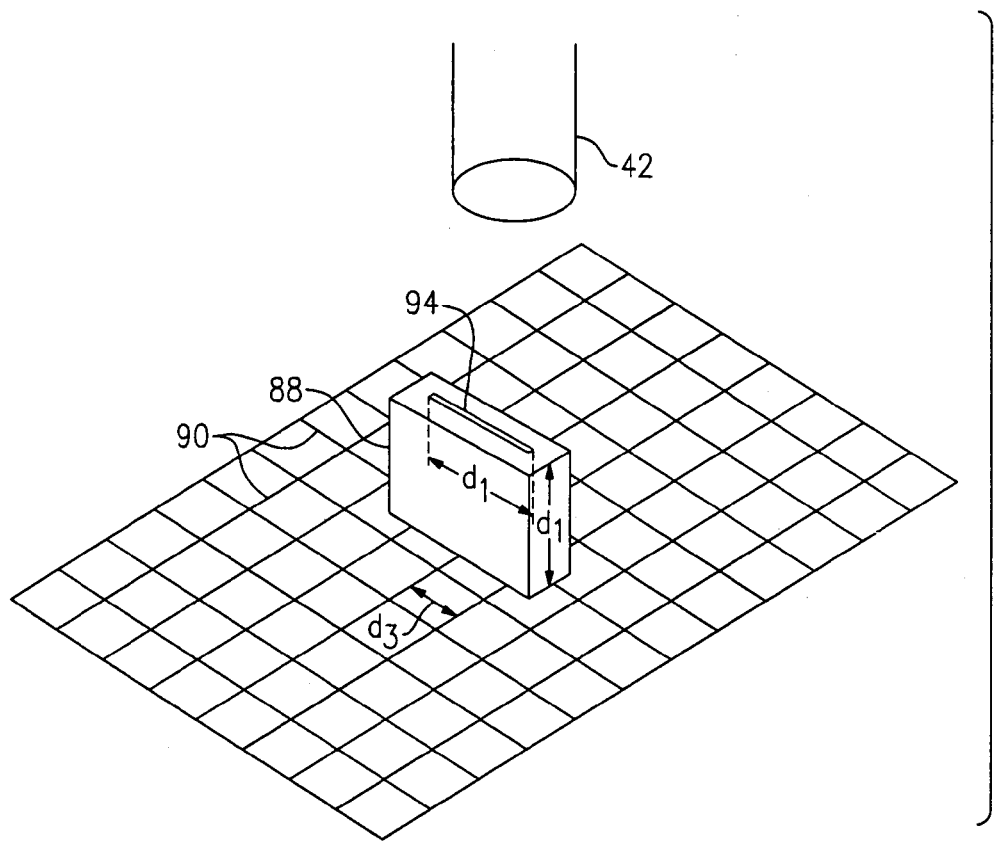
FIG. 18 shows a base of the calibration tool of FIG. 16 with a plurality of grid lines arrayed across an upper surface of the base.

Referring to FIG. 18, a plurality of grid lines 90 of known spacing d3 are on upper surface 86 of base 82. The length of line 94 is a known distance d1, while the height of post 88 is a known distance d2. FIG. 19 shows the view of left and right images 21, 22 of post 88 and surface 86 as displayed on monitor 20 (FIG. 15). Note how grid lines 90 become distorted the further away from post 88 they are. This distortion is known as optical mapping distortion.

Optical data set 70 preferably includes calibration parameters pertaining to (a) optical mapping distortion, (b) magnification at a particular object distance, and (c) left to right image shift vs. object distance, i.e., parallax information. These calibration parameters can be determined using calibration tool 80.

In the preferred embodiment, a calibration process executed by CPU 56 automatically locates gridlines 90. Equations are generated which characterize the grid lines. These equations are stored in optical data set 70. Compensation equations are then generated which are used to correct the optical mapping distortion giving a grid with equally-sized squares regardless of position in the image. The process then automatically identifies line 94. The distortion correction equations are used to correct the positions of the endpoints of line 94. Given the distortion-corrected length of d1, the distortion-corrected grid spacing d3, and known height d2, the actual object distance from the effective optical origin to surface 86 is computed. This object distance and the absolute magnification determined from known spacing d3 are stored in optical data set 70. Optionally, if a single point on the top of post 88 is used in conjunction with distances d2 and d3, as long as either the tip to post or tip to grid distance is known.

Finally, the left to right image shifts between the distortion-corrected gridlines on surface 86 and the distortion-corrected endpoints of line d1 are used in conjunction with the computed object distances to surface 86 and the top of post 88 to compute the left to right image shift vs. distance. This parameter is then stored in optical data set 70. It is also possible to store the positions of the automatically identified points in optical data set 70 and compute the relevant optical parameters from those positions when measurements are performed.

Definition of Variables:

Near_OD=object distance to line 94

Far_OD=object distance to gridlines 90 d1_pixels=distortion-corrected length of line 94 in image in pixels d3_pixels=distortion corrected gridline spacing in image in pixels Close_shift=difference in the distortion corrected horizontal positions of points on line 94 as they appear in the left and right image parts in pixels, i.e., horizontal shift.

Far_shift=difference in the distortion corrected horizontal positions of points on gridlines 90 between the left and right image parts in pixels, i.e., horizontal shift.

P=parallax constant

Far_OD/Near_OD=(d1_pixels/d1)/(d3_pixels/d3)

Far_OD=Near_OD*(d1_pixels/d1)/(d3_pixels/d3)

Far_OD=Near_OD+d2

Near_OD*((d1_pixels/d1)/(d3_pixels/d3)−1)=d2

Near_OD=d2/((d1_pixels/d1)/(d3_pixels/d3)−1)

Far_OD=Near_OD+d2

P=Near_OD*((Far_shift−Near_shift)/2)/(Near_OD/Far_OD−1)

The magnification in pixels/unit length and object distance at either line 94 or gridlines 90 are saved as the magnification at a particular distance.

This method of calibration offers a number of advantages over traditional methods. Computing the object distances to the surfaces is preferred over using the by-design or typical object distances because it eliminates errors caused by fixture and optical system manufacturing tolerances as well as imperfect seating of the tip in cavity 92. Optical mapping distortion is directly measured rather than relying on by-design or typical values. This is especially important given the complexity of the distortions generated by wide field-of-view lens system 16 and prism 14 having steep surface angles combined with mechanical alignment tolerances. Determining all parameters from a single captured image rather than, for example, one image for distortion mapping and another for magnification and parallax, eliminates errors that are induced by capturing the two images from slightly different viewing angles or with the detachable tip position shifted slightly relative to the optics in the probe tip. Combined with automatic point and line identification, using a single fixture and image also makes the calibration process simple and inexpensive enough to allow users to perform the calibration with new detachable tips themselves without having to return the probe to the factory.

In an alternative embodiment, a single point on the top of post 88 is used in conjunction with distances d3 and known Near_OD or Far_OD. In this case, P may be computed directly using these dimensions and the distortion corrected pixel locations of the point on post 88 and gridlines 90. This approach provides all the data necessary to perform measurements, but mechanical positioning of the optical system relative to the target points is more critical than with the preferred embodiment.

In probe systems having multiple, individually calibrated, detachable measurement tips, the system must know which tip is currently attached so that the correct optical data set 70 is used for measurements. The user typically must indicate to the system which tip is being used, and it is not unusual for the user to identify the wrong tip. Because different tips have different optical characteristics, the image being used for measurement can be analyzed to be sure it matches the tip that has been identified. With stereo tips, there is typically a vertical offset between the left and right image parts caused by accidental, or possibly intentional, differences in the positioning of optics in the left and right image paths. If the offset detected in the measurement image is different from the offset detected during calibration, the user is optionally notified that the incorrect tip may have been identified. Furthermore, the offset is optionally used to automatically identify the tip being used.

Measuring an object using the calibrated system 40 is preferably performed using the following steps.

1) Using onscreen cursors and user input through joystick 64 and/or keypad 62, identify points in the left image relevant to the measurement.

2) Identify matching points in the right image automatically or manually.

3) Un-distort both the left and right side positions of the identified points using the optical mapping distortion parameters.

4) Find the left/right unit shift for each point pair using the distortion-corrected left and right side point positions.

5) Using the results of step (4), and the shift vs. distance parameter, compute the object distance at each point:

defining Point_OD=object distance to a point on an object and

Point_shift=difference in the distortion corrected horizontal positions of the point as it appears in the left and right image parts in pixels, i.e. horizontal shift, we have Point_OD=P/(P/Far_OD−(Far_shift−Point_shift)/2).

6) Using the results of steps (3) and (5) and the magnification at a given distance parameter, compute the unit magnification at each point:

definingPoint_Mag=magnification in pixels/unit length at the point, we have

Point_Mag=d3_pixels/d3*Far_OD/Point_OD

7) Using the 2-D unit spacing between points, the unit magnifications at each point, and the object distance for each point, compute the 3-D distance between points, using either the left, right, or both images to do so.

This basic process can be extended to include more than two points in various combinations to measure more complex geometries such as areas, volumes, distances between combinations of points, lines, and planes, angles between lines and/or planes and the like.

The unit spacing is preferably in terms of pixels, while the unit magnification is preferably in terms of mm per pixel or inches per pixel, although other units may be used. The measurement process is preferably carried out in software residing in program memory 58 (FIG. 15), but is optionally implemented in hardware or firmware.

Figure 20A:
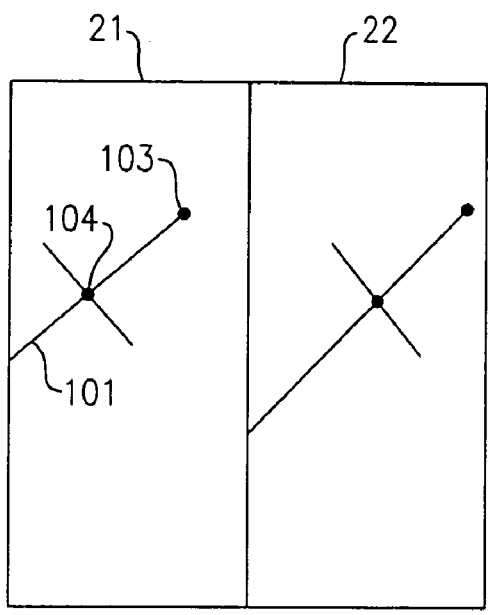
FIG. 20A shows a stereo image of part of an object used in explaining a feature of the invention.
Figure 20B:
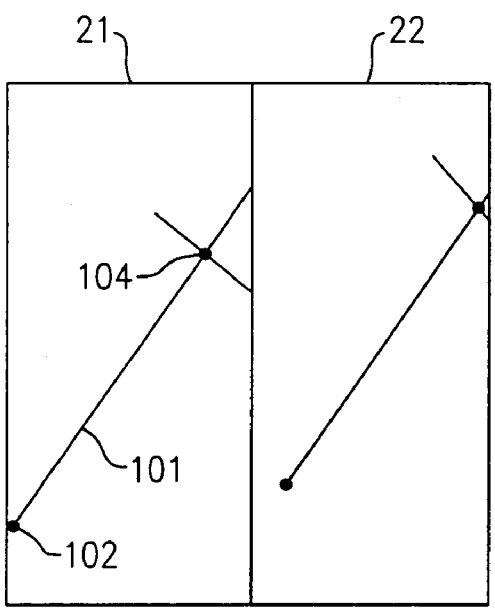
FIG. 20B shows a stereo image of another part of the object partially shown in FIG. 20B.

Referring to FIGS. 20A–20B, when an object spans more than one field of view, two or more stereo images are used to perform measurements. An object 101 is shown which extends from a point 103 (FIG. 20A) to a point 102 (FIG. 20B). A point 104 is an intermediate point between point 103 and point 102 which is visible in the left and right images of both FIGS. 20A and 20B. The distance from point 104 to point 103 (FIG. 20A) is measured and added to the distance from point 104 to point 102 (FIG. 20B) to obtain the total distance for object 101. The procedure is preferably carried out using as many different views as necessary to obtain the complete geometric characteristics of the object. In the preferred embodiment, the user identifies only end points 102 and 103. The system then automatically identifies intermediate points, such as point 104, in each of the images.

Figure 21:
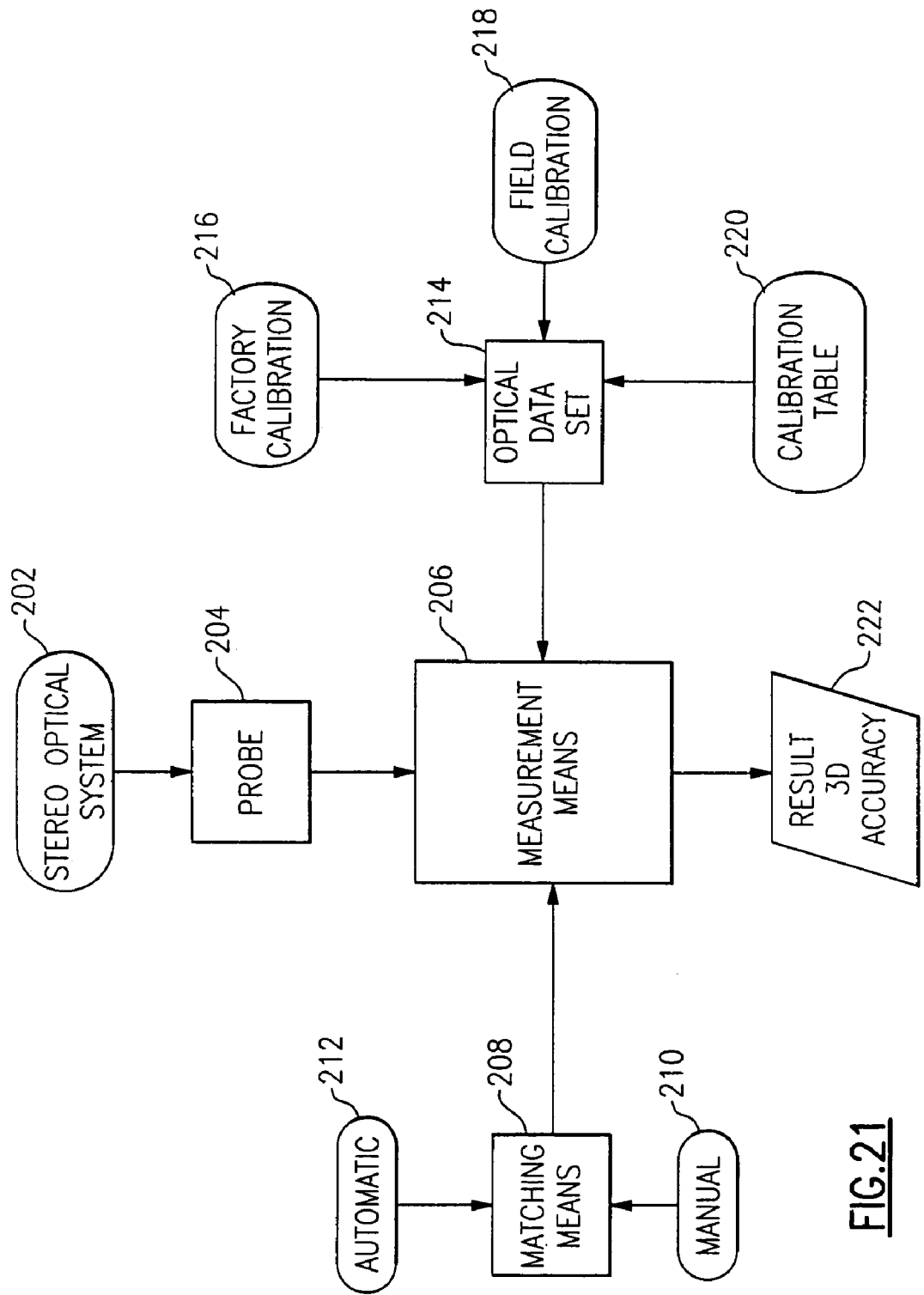
FIG. 21 shows a functional connection of the parts of an embodiment of the stereo borescope/endoscope system.

Referring to FIG. 21, a functional connection of the parts of an embodiment of the stereo borescope/endoscope system is shown. A stereo optical system 202, optionally implemented in a detachable tip, is combined with a probe 204. A measurement means 206 receives stereo images from probe 204 and begins the measurement process. The measurement means preferably uses a matching means 208 to match points on the left and right stereo images. The matching is done either manually (210), automatically (212), or with a combination of manual and automatic techniques. The measurement means also preferably uses an optical data set 214 which is generated by factory calibration 216, field calibration 218, or a calibration table 220. Measurement means 206 then produces outputs 222 which preferably includes a measurement result, 3-D data about the object, and information concerning the accuracy of the measurements.

It is often desirable to transfer measurement images from borescope/endoscope system 40 to a computer for re-measurement, possibly by an individual with more expertise than the user who captured the image. To perform re-measurement, it is necessary to have both the image and optical data set 70. Saving the image and the optical data set in separate files creates a risk that the wrong optical data set will be used for re-measurement or that the two files will become separated making re-measurement impossible. The image and optical data set, possibly along with data pertaining to any measurements that have already been performed, are preferably saved in a single file for later use as described in U.S. Provisional Application Ser. No. 60/270,967 filed Feb. 22, 2001 and entitled METHOD FOR STORING CALIBRATION DATA WITHIN IMAGE FILES, incorporated herein by reference. This approach assures that the correct optical data set is used for re-measurement and prevents the separation of the optical data set from the image data.

In another embodiment of the invention, a plurality of points in a given area, i.e., the stereo left/right pairs, are assembled and three dimensional information derived from the points is structured into a finished file which permits reconstructing at least one geometric characteristic of the image. Such a file could be a 3D CAD file, contour map file, grid file, or a wire frame file. The more complicated the surface being viewed, the more points required to produce an accurate model. Geometric characteristics include such items as length, area, volume, angle, and the like.

Figure 22A:
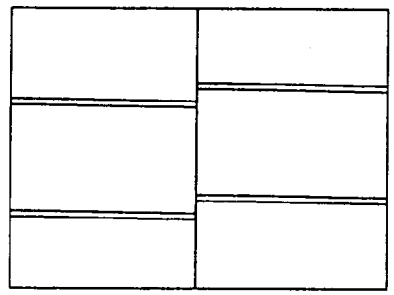
FIG. 22A shows a stereo image with a pair of horizontal lines on which individual point matching is very difficult or impossible.
Figure 22B:
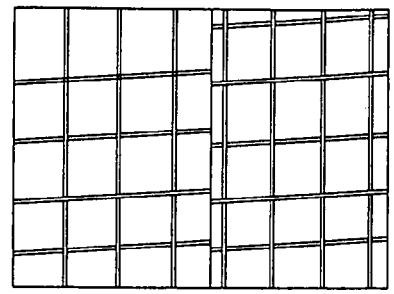
FIG. 22B shows a stereo image with a grid which creates a high probability of incorrect point matching.
Figure 23A:
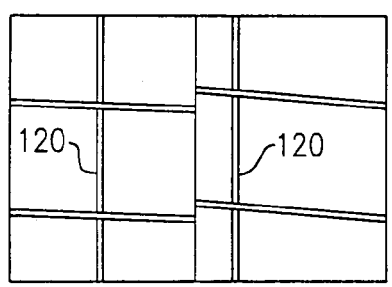
FIG. 23A shows the image of FIG. 22A with the addition of a shadow line.
Figure 23B:
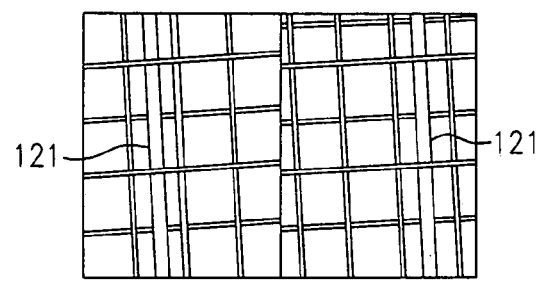
FIG. 23B shows the image of FIG. 22B with the addition of a shadow line.
Figure 26:
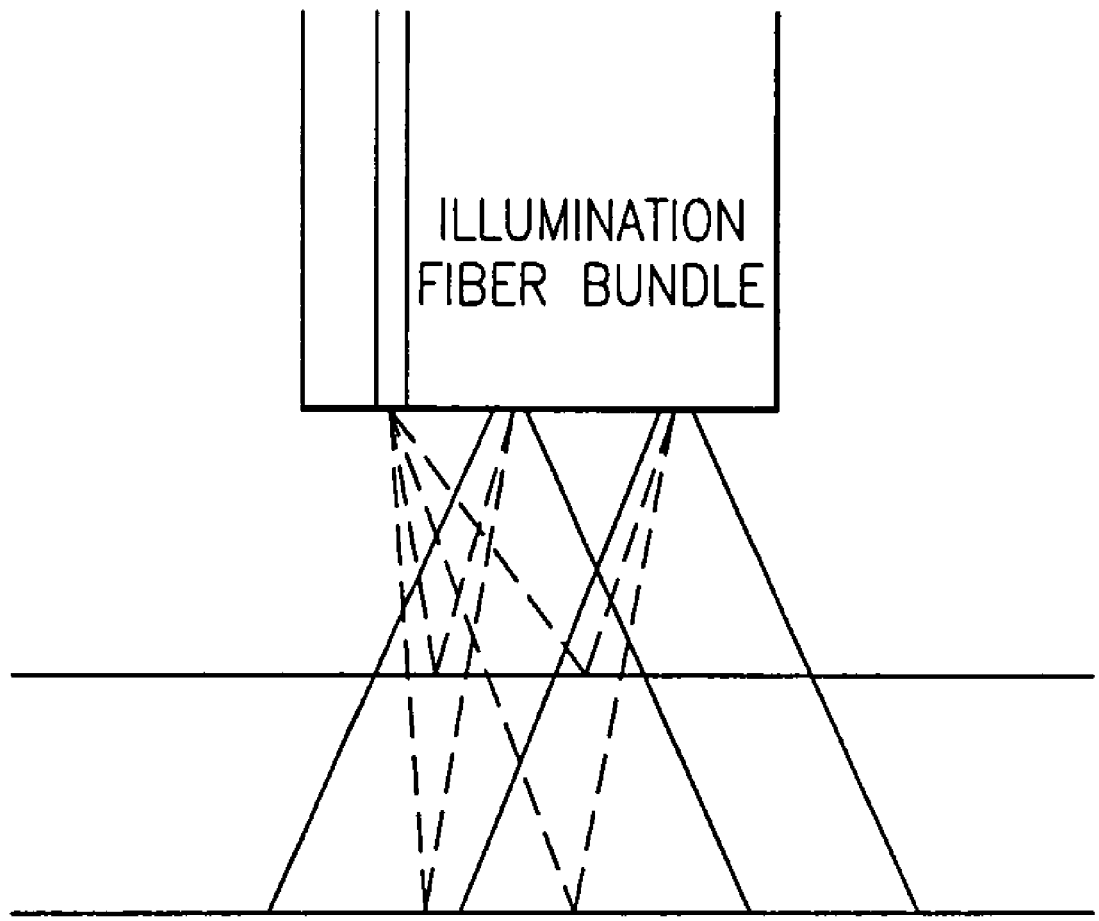
FIG. 26 shows how the reflection of the illumination fiber bundle changes position based on the distance to the reflective surface.

In another embodiment of the invention, the measuring process includes projecting a pattern from an off-imaging axis onto the object being viewed such that the pattern tracks across the object relative to a distance of the object from the device, and using a location of the pattern on the object to aid determination of the measurement data. In some cases, the projected pattern can provide a unique feature to improve the accuracy of the point matching process. FIG. 22A shows a stereo image of a pair of horizontal lines. Matching individual left/right points on the lines is difficult or impossible due to the lack of unique details along the lines. FIG. 22B shows a stereo image of a grid. The repeating pattern of the grid creates a high risk of incorrect left/right point matching. In FIG. 23A and FIG. 23B, projected shadow lines 120 and 121 are added to the images. In FIG. 23A, the points where shadow line 120 crosses the horizontal lines can now be accurately matched allowing the line spacing to be measured. In FIG. 23B, assuming a limited global vertical shift, alignment of the gridlines on the left and right sides is made clear, greatly reducing the risk of incorrect point matching. These embodiments are enabled by the disclosures in U.S. Pat. No. 4,980,763 (Lia) and U.S. Pat. No. 5,070,401 (Salvati et al.), both of which are incorporated herein by reference. These embodiments are preferably used in conjunction with the measuring process described above to enhance the process. On many surfaces, a reflection of the light fiber bundle from the surface can be detected. As shown in FIG. 26, the position of this reflection in the left and right images varies with the object target distance, so the reflection could also be used in the stereo measurement process.

In another embodiment of the invention, multiple images of an object to be measured are captured from different perspectives. The user then identifies the points relevant to the measurement in one image. The point matching process is used to find automatically the same left and right side points in the other captured images, with the result being computed from each image. The multiple results are then combined to produce a final result that is likely to be more accurate than any of the individual measurements.

Figure 24:
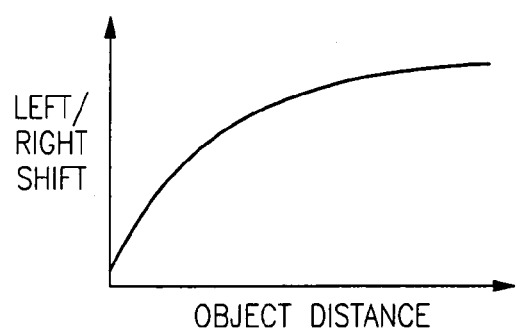
FIG. 24 shows the relationship of left/right shift vs. object distance.
Figure 25:
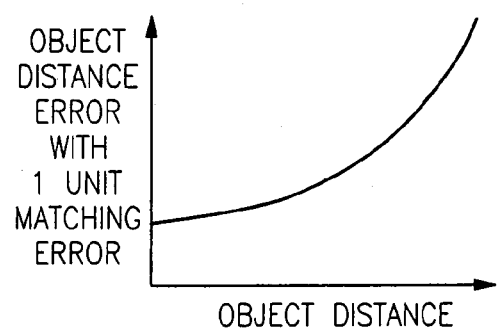
FIG. 25 shows the object-distance error caused by a unit error in left/right shift.

The accuracy of the measurements performed is dependent on several factors including object distance, image resolution, distortion correction accuracy, and point matching accuracy. As shown in FIG. 24, the left/right shift changes considerably with a unit change in object distance at close object distances. At larger object distances, the left/right shift changes much less for the same unit change in object distance. This means that the impact of a 1 unit error in left/right shift, caused by imperfect distortion correction and/or matching, increases with object distance. This increase is exponential in nature as illustrated in FIG. 25. A combination of computed object distance, image resolution, point matching sureness, and typical distortion correction accuracy is preferably used to estimate the unit accuracy tolerance of the measurement. This unit tolerance combined with the measurement result provides a percent accuracy tolerance. Either of these measures or another measure derived from these measures is preferably displayed to the user. Allowing the user to set a maximum tolerance limit, above which a visual or audible notification is made, reduces the likelihood that an unacceptably-large tolerance will go unnoticed.

In another embodiment of the invention, the object distance, as determined by the measurement process, is used to select a point-spread function (PSF) which accurately characterizes the blurring effects of the optical system when viewing objects at that object distance. Deconvolution techniques are then used to reverse these blurring effects yielding a more in-focus image than otherwise.

Figure 27:
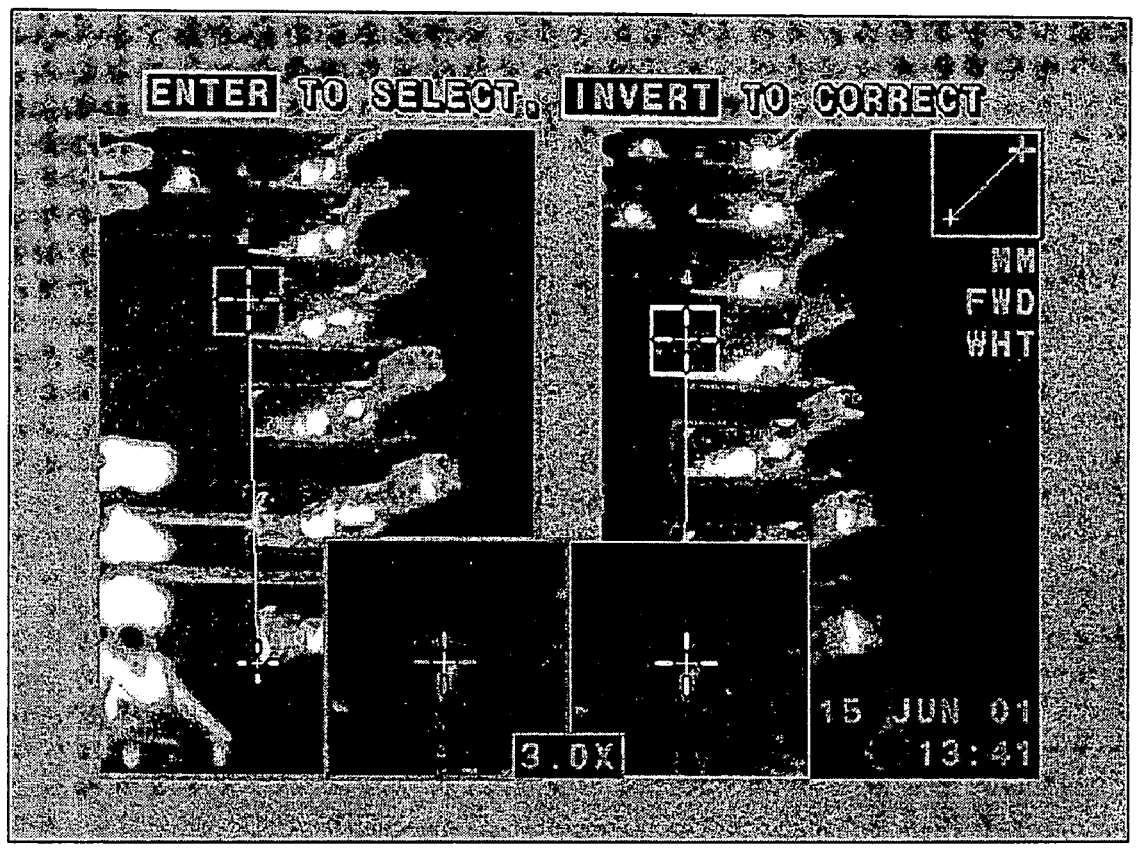
FIG. 27 shows the use of small zoomed views concurrently with the unzoomed stereo image.

Referring to FIG. 27, accurate placement of the measurement cursors and matching of the identified points are critical to achieving measurement accuracy. It can be difficult, especially with small monitors, to make accurate cursor placements and to verify accurate matching. One solution is to zoom the entire image so that the area around the cursor is seen more easily. This approach, however, typically hides a portion of the image. If a repeating pattern exists, it is sometimes impossible to tell where in that pattern the cursor is positioned. FIG. 27 shows the concurrent display of the main left and right images along with smaller zoomed windows showing the left and right cursor positions in much greater detail. In this way, the position within repeating patterns is still visible while making accurate cursor placement and matching verification much easier. Alternatively, the area surrounding only the user-designated cursor is optionally shown in a smaller zoomed window to reduce processing time and/or display area usage.

It is important for the user to verify that the automatic point matching function properly identifies the match in the right image. In other systems, the user must position a cursor in the left image and then press a button before the automatic matching of the point begins. The system will then typically go on to the placement of the next cursor in the measurement. If the match is incorrect, the user must then take other steps to either correct the match or to select and move the left cursor to see if the system can match a slightly different point.

According to the present invention, a preferred method is to start the automatic match as soon as movement of the left cursor stops. This way, the user can see if the match is correct without any other input. If the match is incorrect, the user can immediately move the cursor again to see if a correct match is achieved with a slight change in position without performing additional steps to activate the cursor that was improperly matched. With a fast enough matching function, the match is performed in real-time as the left cursor is moved, so the user can immediately see if the match is correct.

Figure 28:
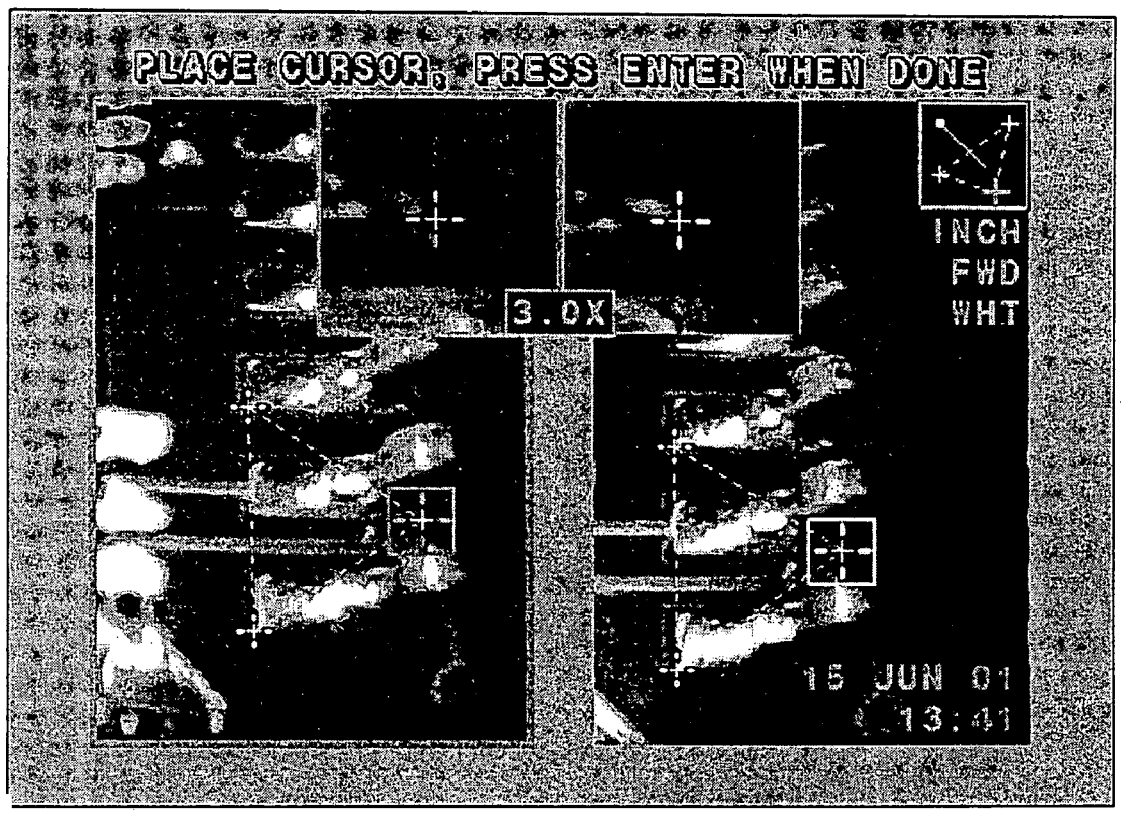
FIG. 28 shows the use of a dynamic icon to help the user step through the measurement process.
Figure 29:
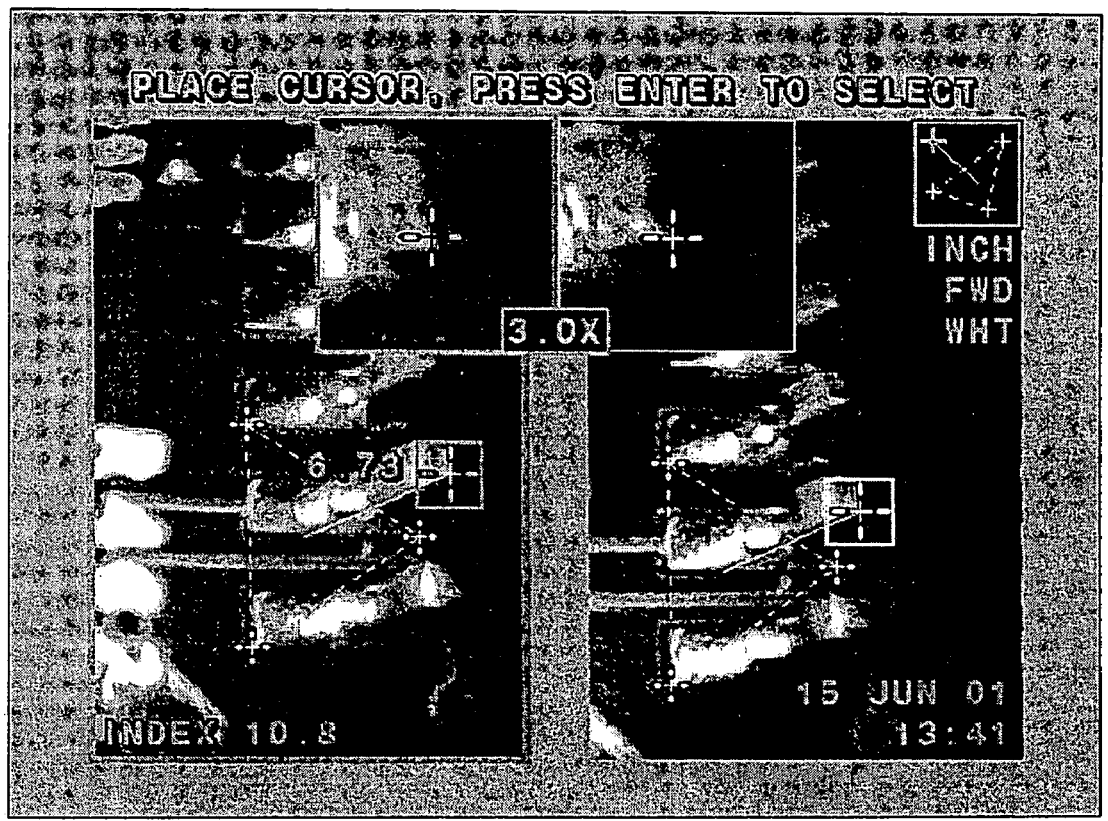
FIG. 29 shows the use of a dynamic icon to help the user step through the measurement process.

Referring to FIGS. 28–29, multiple points must be identified to perform a measurement. When measurements require more than two points, such as in point to line or point to plane measurements, the user must know whether the cursor being placed is used to define the "point", the "line", or the "plane". On-screen instructions tend to be very consuming of display area. Using a single icon which indicates both the type of measurement and how the cursor being placed is used in the measurement allows the same display space to provide both informational items. In FIG. 28, the icon in the upper right corner, and in particular the cross symbol, shows that a point to plane measurement is being performed and that the active cursor is used in the definition of the plane. In FIG. 29, the icon has changed, with the cross symbol showing that the active cursor defines the off-plane point.

When more than one type of measurement is available, it is possible that the user will place one or more cursors before deciding that they would rather perform a different type of measurement. In other systems, changing the measurement type causes the cursors that have been placed to be removed. Often, however, the points that were already placed could have been used with the new measurement type. The user then has to repeat the placement of the lost cursors. According to the present invention, a preferred method is to keep the positions of any usable cursors that have already been placed when the measurement type is changed.

While the present invention has been described with reference to a particular preferred embodiment and the accompanying drawings, it will be understood by those skilled in the art that the invention is not limited to the preferred embodiment and that various modifications and the like could be made thereto without departing from the scope of the invention as defined in the following claims.

What is claimed is:

1. A stereo endoscopic system comprising:
an endoscopic probe;
an electronic imaging device; and
an optical system, each of said electronic imaging device and said optical system being arranged entirely along a single optical axis, said optical system including:
a refractive image splitter and at least one focusing lens disposed between said electronic imaging device and said refractive image splitter, wherein said refractive image splitter directly passes an image of an object of interest to be split along said single optical axis into two images of said object that are guided through said refractive image splitter entirely along said single optical axis to said at least one focusing lens without optical power between the object of interest and said at least one focusing lens, said two images being representative of first and second acquired stereo images of said object of interest that are focused by said at least one focusing lens along said single optical axis onto said electronic imaging device;
wherein said refractive image splitter is a refractive image-splitting prism having a ridge pointing away from said electronic imaging device and a substantially flat base facing said electronic imaging device.

2. A stereo endoscopic system as recited in claim 1, wherein views of said first and second images converge at a given object distance such that said views overlap 100% at said object distance.

3. A stereo endoscopic system as recited in claim 1, wherein said refractive image splitter is contained within a detachable distal tip which is usable with said endoscopic probe.

4. A stereo endoscopic system as recited in claim 1, wherein said first and second acquired stereo images are symmetrical.

5. A stereo endoscopic system as recited in claim 1, further comprising a window disposed between said refractive image splitter and said object, wherein contact is prevented between external media and said image splitter.

6. A stereo endoscopic system as recited in claim 1, further comprising a display for viewing said first and second acquired stereo images as detected by said electronic imager.

7. A stereo endoscopic system as recited in claim 6, wherein only one of said first and second acquired stereo images is displayed.

8. A stereo endoscopic system as recited in claim 6, further comprising viewing means for viewing said first and second images such that said first image goes to a right eye of a viewer, and said second image goes to a left eye of said viewer wherein said viewer is provided with a three dimensional perspective.

9. A stereo endoscopic system as recited in claim 6, including measuring means for comparing parameters of said first and second acquired images such that measurement data of said object is determined, wherein said measurement data includes at least one geometric characteristic of the object, said measuring means including at least one onscreen cursor wherein at least one portion of said first and second acquired stereo images is displayed at a different magnification relative to the displayed first and second images and wherein both said at least one portion and at least one of said first and second acquired stereo images are displayed simultaneously, said at least one portion containing said onscreen cursor for aiding in the real-time positioning of same.

10. A stereo endoscopic system as recited in claim 1, further comprising measuring means for comparing parameters of said first and second images so that measurement data of said object are determined, wherein said measurement data includes at least one geometric characteristic of said object.

11. A stereo endoscopic system as recited in claim 10, further comprising an optical characteristics data set used by said measuring means to determine said measurement data.

12. A stereo endoscopic system as recited in claim 11, wherein a user is signaled that a detachable distal tip emplaced on said probe may have been incorrectly identified if a difference between said optical characteristics data set and global alignment data determined from said image exists.

13. A stereo endoscopic system as recited in claim 11, wherein said system is used in an inspection device, said system further comprising calibration means for generating said optical characteristics data set of said device, wherein said calibration means includes a plurality of object target points at a plurality of object target distances which appear in both of said first and second acquired stereo images when viewed with said probe.

14. A stereo endoscopic system, according to claim 13, wherein said calibration means includes means for color balancing.

15. A stereo endoscopic system as recited in claim 13, wherein said plurality of object target points comprises at least two object target points with known spacing between them at a first object target distance and at least two object target points with known spacing between them at a second object target distance, wherein a distance between said first and second object target distances is known.

16. A stereo endoscopic system as recited in claim 13, wherein said plurality of object target points comprises at least two object target points with known spacing between them at a first object target distance and at least one object target point at a second object target distance, wherein a distance between said first and second object target distances is known, and wherein one of said first and second object target distances is known.

17. A stereo endoscopic system as recited in claim 13, wherein said optical characteristics data set includes optical mapping distortion, magnification at one or more object target distances, and parallax information, wherein said calibration means generates said optical characteristics data set from only one image.

18. A stereo endoscopic system as recited in claim 13, further comprising means for automatic detection and identification of said plurality of object target points.

19. A stereo endoscopic system as recited in claim 13, wherein calibration means includes using a reflection of illumination at at least one known object target distance.

20. A stereo endoscopic system as recited in claim 11, wherein said optical characteristics data set is stored in non-volatile memory in said probe.

21. A stereo endoscopic system as recited in claim 11, wherein said optical characteristics data set and said first and second acquired stereo images are stored in a single file.

22. A stereo endoscopic system as recited in claim 11, adjusting means for adjusting said optical characteristics data set of said device to increase the accuracy of said measurement data when a distal portion of said probe is operated in a medium with an index of refraction which differs from that of air.

23. A stereo endoscopic system as recited in claim 10, wherein said system is adapted for receiving one of a plurality of detachable probe tips, wherein each of said detachable probe tips has a plurality of corresponding optical characteristics data sets, and wherein data determined from said image is used to select which optical characteristics data set corresponds to said detachable probe tip emplaced on said probe.

24. A stereo endoscopic system as recited in claim 23, wherein each of said plurality of detachable probe tips has a plurality of corresponding optical characteristics data sets, and wherein data determined from said image is used to select which optical characteristics data set corresponds to said detachable probe tip emplaced on said probe.

25. A stereo endoscopic system as recited in claim 10, wherein said measuring means includes matching means for matching a same point viewed on said object in each of said first and second acquired stereo images.

26. A stereo endoscopic system as recited in claim 25, wherein said matching means includes automatic matching means for automatic matching of a user designated point viewed on said object in said first image to a corresponding point in said second image.

27. A stereo endoscopic system as recited in claim 26, wherein said automatic matching means includes means for requesting user selection of a correct matched point from a plurality of automatically-identified possible matches.

28. A stereo endoscopic system as recited in claim 26, wherein, when a position of said user-designated point on said viewed object in said first image is changed by said user, said automatic matching dynamically occurs without further user intervention.

29. A stereo endoscopic system as recited in claim 26, wherein said automatic matching means includes global alignment means for performing an automatic global alignment of said first and second acquired stereo images.

30. A stereo endoscopic system recited in claim 29, wherein said global alignment means includes means for determining a global vertical shift between said first and second acquired stereo images.

31. A stereo endoscopic system as recited in claim 29, wherein said global alignment means includes means for automatically determining one or more regional horizontal shifts between said first and second images.

32. A stereo endoscopic system as recited in claim 29, wherein said global alignment means uses the positions of one or more user-designated matched points in said first and second acquired stereo images to aid in performing said global alignment.

33. A stereo endoscopic system as recited in claim 29, wherein a correction by a user of an incorrect automatic match automatically invokes said global alignment means.

34. A stereo endoscopic system as recited in claim 29, wherein data derived from said global alignment means is used to make said automatic matching of said matching means faster than otherwise.

35. A stereo endoscopic system as recited in claim 29, wherein data derived from said global alignment means is used to reduce a probability of incorrect matches of subsequent user-defined points.

36. A stereo endoscopic system as recited in claim 29, further comprising means, based on data derived from said global alignment means, for determining and conveying to a user an overlap region of said first and second acquired stereo images in which measurements are performed.

37. A stereo endoscopic system as recited in claim 10, wherein said measuring means includes means for indicating a measurement accuracy of said measurements, wherein said measurement accuracy is determined based at least on object distance.

38. A stereo endoscopic system as recited in claim 37, wherein said measuring means includes means for an operator to designate a maximum estimated error limit for said measurement accuracy above which said device indicates a warning.

39. A stereo endoscopic system as recited in claim 10, wherein said measuring means includes using at least one onscreen cursor and means for displaying a symbol, which indicates both a type of measurement being performed and a role of said cursor in said type of measurement.

40. A stereo endoscopic system as recited in claim 10, wherein said measuring means includes using at least one onscreen cursor and wherein at least one measurement point designated by a user when performing one type of measurement is kept even when a different type of measurement is selected.

41. A stereo endoscopic system as recited in claim 10, wherein said determined measurements are stored as non-viewable data along with said images in a single file.

42. A method for creating stereo images using an endoscope for use in imaging and measuring a defect of an object, said method comprising the steps of:
splitting a view of the object of interest viewed with the endoscope into first and second images of said object using a refractive image splitter disposed along a single optical axis, wherein a single image of the object is transmitted to said image splitter, said first and second images being intermixed through said image splitter and transmitted to at least one focusing lens disposed along said single optical axis without optical power being applied between an object plane and said at least one focusing lens, and wherein said refractive image splitter is a refractive image-splitting prism having a ridge pointing away from an electronic imaging device and a substantially flat base facing said electronic imaging device;

focusing said first and second images from said refractive image splitter onto said electronic imager disposed along said single optical axis; and detecting said first and second adjacent images using said electronic imager for display thereof.

43. A method as recited in claim 42, further comprising the step of comparing parameters of said first and second acquired stereo images to determine measurement data of said object.

44. A method as recited in claim 43, further comprising the step of generating an optical characteristics data set of said endoscope by comparing a known set of object target points at a plurality of object target distances.

45. A method as recited in claim 44, further comprising the step of using said optical characteristics data set to determine said measurement data.

46. A method as recited in claim 44, further comprising the step of storing said optical characteristics data set in non-volatile memory in said probe.

47. A method as recited in claim 44, further comprising the step of adjusting said optical characteristics data set so that said probe is operable in a medium with an index of refraction other than air.

48. A method as recited in claim 44, wherein said step of generating an optical characteristics data set includes color balancing.

49. A method as recited in claim 44, wherein said set of known object target points comprises at least two object target points at a first object target distance and at least one object target point at a second object target distance.

50. A method as recited in claim 44, further comprising generating said optical characteristics data set from said first and second acquired stereo images, wherein said optical characteristics data set includes optical mapping distortion and magnification at one or more object target distances.

51. A method as recited in claim 44, further comprising the step of automatically detecting and identifying said known set of object target points.

52. A method as recited in claim 44, wherein said step of generating said optical characteristics data set includes using a reflection of illumination at at least one known object target distance.

53. A method as recited in claim 43, further comprising the step of matching a same point in each of said first and second images.

54. A method as recited in claim 53, further comprising the step of automatically matching a user designated point from said first image to said second image.

55. A method as recited in claim 54, wherein said step of automatically matching includes performing a global alignment of said first and second acquired stereo images.

56. A method as recited in claim 55, wherein said step of performing said global alignment includes determining a global vertical shift between said first and second acquired stereo images.

57. A method as recited in claim 55, wherein said step of performing said global alignment includes determining one or more regional horizontal shifts between said first and second acquired stereo images.

58. A method as recited in claim 55, wherein data derived from the step of automatically matching at least one matched point in said images is used to make the step of automatically identifying at least one user defined point from said first image to said second image complete faster than otherwise.

59. A method as recited in claim 53, wherein said step of matching includes the step of automatically identifying at least one matched point in said first and second acquired stereo images.

60. A method as recited in claim 59, wherein data derived from the step of automatically identifying at least one matched point in said first and second acquired stereo images is used to reduce a probability of incorrect matches of subsequent user-defined points.

61. A method as recited in claim 59, further comprising the step of determining and conveying to a user an overlap region of said first and second acquired stereo images in which measurements are performed.

62. A method as recited in claim 43, wherein the step of comparing parameters includes the step of indicating a measurement accuracy of said measurements, wherein said measurement accuracy is determined based at least on object distance.

63. A method as recited in claim 62, wherein the step of comparing parameters includes enabling an operator to designate a maximum estimated error limit for said measurement accuracy above which limit said device indicates a warning to said operator.

64. A method as recited in claim 43, wherein the step of comparing parameters includes using at least one onscreen cursor.

65. A method as recited in claim 43, further comprising the step of storing said determined measurements as non-viewable data along with said images in a single file.

66. A method as recited in claim 42, further comprising the step of determining at least one geometric characteristic of said object.

* * * * *